(12) United States Patent
Thorne, Jr. et al.

(10) Patent No.: US 6,358,265 B1
(45) Date of Patent: Mar. 19, 2002

(54) SINGLE-STEP DISPOSABLE SAFETY LANCET APPARATUS AND METHODS

(75) Inventors: Gale H. Thorne, Jr., Bountiful; Michael A. Wilson, Salem; Charles V. Owen, Highland; David L. Thorne, Kaysville; B. Chance Bagley, Ogden, all of UT (US)

(73) Assignee: Specialized Health Products, Inc., Bountiful, UT (US)

( * ) Notice: Subject to any disclaimer, the term of this patent is extended or adjusted under 35 U.S.C. 154(b) by 41 days.

(21) Appl. No.: 09/619,043

(22) Filed: Jul. 18, 2000

(51) Int. Cl.[7] .............................................. A61B 17/32
(52) U.S. Cl. .................................................... 606/181
(58) Field of Search .................... 606/181, 182, 606/185; 604/198, 192, 263; 30/340, 342

(56) References Cited

U.S. PATENT DOCUMENTS

| | | | |
|---|---|---|---|
| 3,262,448 A | 7/1966 | Ring .......................... 128/214 |
| 3,262,449 A | 7/1966 | Pannier | |
| 3,344,786 A | 10/1967 | Berg .......................... 128/215 |
| 3,438,373 A | 4/1969 | Pannier | |
| 3,463,152 A | 8/1969 | Sorenson | |
| 3,491,756 A | 1/1970 | Bentov | |
| 3,809,081 A | 5/1974 | Loveless ..................... 128/214 |
| 3,923,066 A | 12/1975 | Francisoud ................. 128/348 |
| 4,157,086 A | 6/1979 | Maiorano .................... 128/637 |
| 4,233,975 A | 11/1980 | Yerman ....................... 128/218 |
| 4,274,408 A | 6/1981 | Nimrod ....................... 128/214 |
| 4,417,886 A | 11/1983 | Frankhouser ............... 604/53 |
| 4,509,945 A | 4/1985 | Kramann ..................... 604/164 |
| 4,525,157 A | 6/1985 | Vaillancourt ................. 604/52 |
| 4,529,399 A | 7/1985 | Groshong .................... 604/53 |
| 4,539,988 A | 9/1985 | Shirley ....................... 128/314 |
| 4,627,445 A | 12/1986 | Garcia ........................ 128/770 |
| 4,637,403 A | 1/1987 | Garcia ........................ 128/770 |
| 4,643,189 A | 2/1987 | Mintz ......................... 128/314 |
| 4,652,256 A | 3/1987 | Vaillancourt ................. 604/52 |
| 4,735,203 A | 4/1988 | Ryder ......................... 128/314 |
| 4,772,264 A | 9/1988 | Cragg ......................... 604/158 |
| 4,828,547 A | 5/1989 | Sahi ............................ 604/110 |
| 4,832,693 A | 5/1989 | Gloyer ........................ 604/110 |
| 4,832,696 A | 5/1989 | Luther ........................ 604/164 |
| 4,892,097 A | 1/1990 | Ranalletta ................... 606/182 |
| 4,995,402 A | 2/1991 | Smith ......................... 128/771 |
| 5,009,642 A | 4/1991 | Sahi ............................ 604/158 |
| 5,047,044 A | 9/1991 | Smith ......................... 606/182 |
| 5,133,730 A | 7/1992 | Biro ............................ 606/182 |
| 5,196,025 A | 3/1993 | Ranalletta ................... 606/182 |
| 5,314,441 A | 5/1994 | Cusack ....................... 606/182 |
| 5,318,583 A | 6/1994 | Rabenau ..................... 606/182 |
| 5,356,420 A | 10/1994 | Czernecki ................... 606/182 |
| 5,395,388 A | 3/1995 | Schraga ...................... 606/182 |
| 5,439,473 A | 8/1995 | Jorgensen ................... 606/182 |
| 5,476,474 A | 12/1995 | Davis .......................... 606/182 |
| 5,514,152 A | 5/1996 | Smith ......................... 606/182 |
| 5,527,334 A | 6/1996 | Kanner ....................... 606/182 |
| 5,569,286 A | * 10/1996 | Peckham et al. ........... 604/192 |
| 5,571,132 A | 11/1996 | Mawhirt ..................... 606/182 |
| 5,584,846 A | * 12/1996 | Mawhirt et al. ............ 606/181 |
| 5,645,555 A | 7/1997 | Davis .......................... 606/182 |
| 5,755,733 A | 5/1998 | Morita ........................ 606/182 |
| 5,823,997 A | 10/1998 | Thorne ........................ 604/110 |

FOREIGN PATENT DOCUMENTS

EP       0 365 196       4/1990    ............ A61B/5/14

* cited by examiner

Primary Examiner—Kevin Truong

(57) ABSTRACT

Three embodiments of a single-step lancet are disclosed. Each such lancet embodiment provides true one-step operation. In a single operational step requiring only a unidirectional displacement of an actuator into a housing, a lancet blade is removed from an aseptic environment which protects and retains the lancet blade in a pre-sterilized state within the housing prior to use, stores energy in an energy storage medium, activates the lancet blade to perform a lance and for safety retracts the lancet blade into the housing.

6 Claims, 26 Drawing Sheets

SINGLE-STEP DISPOSABLE SAFETY LANCET APPARATUS AND METHODS

FIELD OF INVENTION

This invention relates generally to disposable, single-use lancet assemblies and methods, a lancet assembly being used for percutaneous entry into a body segment, such as pricking a finger to collect a small blood sample. More specifically, this invention relates to lancet assemblies which are totally self-contained and packaged as presterilized devices and which require but one operational step to ready a device for use and for performing a lancing operation.

DESCRIPTION OF RELATED ART

Contemporary wide, high volume use of lancets to acquire blood samples from fingers and other body donor sites has resulted in conceptualization, design and development of a large variety of single-use lancet assemblies. Historically, commercial viability of lancets is based upon device cost, device safety, device efficacy (effectiveness of achieving desired blood volume from a patient sample) and level of pain of lancing. As an example, the earliest and likely lowest cost lancet was made from a simple sharpened blade by which a lancing procedure was manually administered by a medical attendant or self-administered by a patient. Even though a sizeable number of such lancets are still being used, considerations of safety (e.g. potential of inadvertent sticks by previously used and contaminated lancets) and associated pain levels have resulted in displacement of simpler, low-cost blades with safer, single-use devices, and especially those which are generally considered to be less painful.

Even so, lancet and associated lancing costs have remained important product selection factors. From a broad view, lancing cost includes far more than cost of the lancet, itself (although lancet cost must be considered as a primary selection criteria). Other costs which are important, especially in the hospital, clinic, doctor's office and other like places where medicine is practiced, are associated with convenience or ease of use and numbers of residual parts which must be gathered up and disposed of at the end of each procedure. While such factors may seem insignificant, lancets which require, for example, protection by a blister pack have commonly been displaced by devices which do not require additional packaging.

One of the common methods for eliminating the need for external packaging has been development of removable sterile covers which protect just the lancing blade and are easily removed immediately before lancet use. Such a method is disclosed in U.S. Pat. No. 5,755,733 issued May 26, 1998 to Susumu Morita (Morita). Morita discloses a lancet blade which is over-molded with a removable sterile covering. In this manner, a blade, once sterilized, remains uncontaminated until the covering is removed. However, even the device disclosed by Morita requires an operational step to remove the covering prior to use and, then, disposal of the small covering, which may prove to be hazardous if inadvertently left in such places as children's and pediatric units, after a procedure.

BRIEF SUMMARY AND OBJECTS OF THE INVENTION

In brief summary, this novel invention alleviates all of the known problems related to providing a true single-step, disposable lancet. Lancet devices made according to the instant invention comprise a housing and a lancet blade, which may be of a blade or pin format or any other form which yields acceptable amounts of blood flow. Such a device also comprises an energy storing member which is preferably kept in a relaxed state for transport and storage prior to use, although the state of the energy storing member is not an essential part of the invention.

Lancets made according to this invention are true single-step lancets whereby the entire lancing procedure involves but a single operational step. For example, there is no external package or blade cover which requires an additional step to remove a lancet blade covering. The single step operation lancet is accomplished without degrading or comprising device sterility, and lancet actuation is accomplished by a single unidirectional motion. Such motion separates the lancet blade from a protective cover and actuates the lancet. If the energy storing member is kept in a relaxed state prior to actuation, energy which is stored to drive the lancet blade is supplied by the same unidirectional motion.

In a preferred embodiment of the instant invention disclosed herein, an orifice through which a lancet blade passes to lance is substantially blocked prior to device actuation and cleared by displacing an orifice covering or blocking apparatus during actuation to assure creation of an unobstructed (clean) pathway for the blade. Preferably, the sterility maintaining cover, disposed about the blade prior to actuation, is displaced relative to the blade and separated from the blade in preparation for firing, in such a manner as, to sweep undesirable contaminants from the pathway of the blade.

In all embodiments, such devices are fabricated using a housing, an energy storing member, to which is generally affixed a lancet blade, and an actuator, the actuator being displaceable in a single direction relative to the housing.

Accordingly, it is a primary object to provide a self-contained lancet which requires but one operational step to perform a lancing procedure, the lancet comprising:

a housing comprising an elongated contiguous side wall which surrounds and shelters lancet parts residing within the housing, the housing further comprising an open first end wherethrough an actuator is unidirectionally displaced to energize and activate a lancing cycle and a slot on the other end through which a lancet blade is displaced;

the lancet blade, disposed within the housing for transport before use and for disposal after use;

a lancet blade covering, removable by action of the single operational step, being disposed within the housing to provide a sterile encasement about the lancet blade before use, the covering maintaining the lancet blade in an uncontaminated state until the lancet is uncovered therefrom;

the actuator which is displaceable from a first state, whereat digital access is provided, toward and to a second state whereby the lancet is activated;

an energy storing member which communicates with the actuator at a first site and is securely affixed to the lancet blade at a second site and which stores energy during a first portion of actuator displacement from the first state to the second state and is released during a second portion of actuator displacement from the first state to the second state to discharge the lancet outward from the housing and then to return the lancet to protective safety of the housing; and apparatus which assures separation of the lancet blade from the removable covering during the first portion of displacement of the actuator.

It is a further object to provide a self-contained lancet having apparatus for clearing undesirable material from the region of the slot within the housing to clear an unobstructed pathway for the lancet blade.

It is an object to provide a method for using a self-contained lancet which requires but one operational step to perform a lancing procedure, comprising the steps of:

providing the self-contained lancet comprising:

a housing comprising an elongated contiguous side wall which surrounds and shelters lancet parts residing within the housing, the housing further comprising an open first end wherethrough an actuator is unidirectionally displaced to energize and activate a lancing cycle and a slot on the other end through which a lancet blade is displaced;

the lancet blade, disposed for transport before use and for disposal after use, within the housing;

a covering, removable by action of the single operational step, disposed within the housing to provide a sterile encasement about the lancet blade before use, the covering maintaining the lancet blade in an uncontaminated state until the lancet is separated therefrom;

the actuator which is displaceable from a first state whereat digital access is provided toward and to a second state whereby the lancet is activated;

an energy storing member which communicates with the actuator at a first site and is securely affixed to the lancet blade at a second site and which stores energy during a first portion of actuator displacement from the first state to the second state and is released during a second portion of displacement from the first state to the second state to discharge the lancet outward from the housing and then to return the lancet to protective safety of the housing; and apparatus which assures separation of the lancet blade from the removable covering during the first portion of actuator displacement;

displacing the actuator unidirectionally from the first state to the second state thereby in seriatim storing energy in the energy storing member and separating the lancet blade from the removable covering during the first portion of actuator displacement from the first state to the second state and then releasing the energy storing member at the end of the second state of actuator displacement thereby permitting energy stored in the energy storing member to discharge the lancet from the housing and return the lancet into the housing.

It is a further object to provide a method for using a self-contained lancet which comprises additional steps of providing apparatus for clearing undesirable material within the housing from the region of the slot to clear an unobstructed pathway for the lancet blade and sweeping or otherwise clearing unwanted material from the region of the slot during the first portion of displacement of the actuator from the first state to the second state.

These and other objects and features of the present invention will be apparent from the detailed description taken with reference to accompanying drawings.

DETAILED DESCRIPTION OF THE ILLUSTRATED EMBODIMENTS

Figure 25:
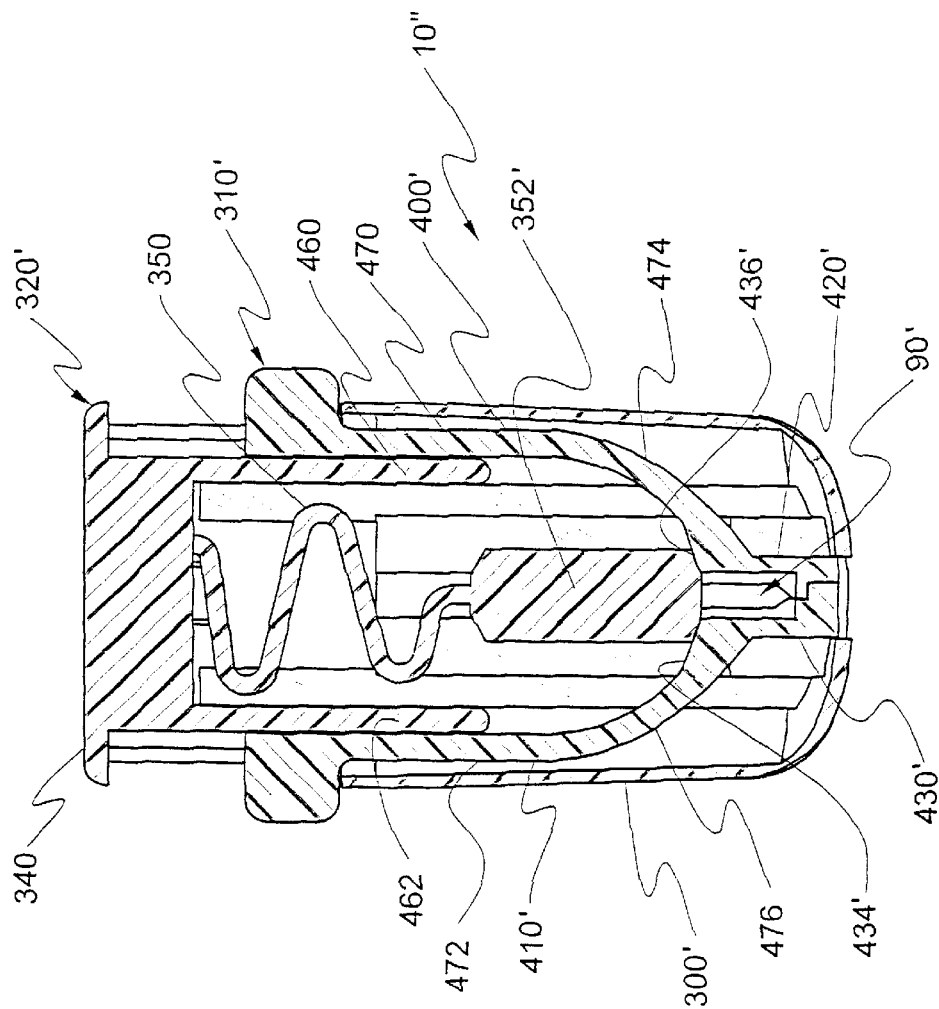
FIG. 25 is a cross section of a third embodiment of a lancet which is made in accordance with the present invention, the embodiment being similar in position and physical characteristics to the lancet seen in FIG. 17.
Figure 26:
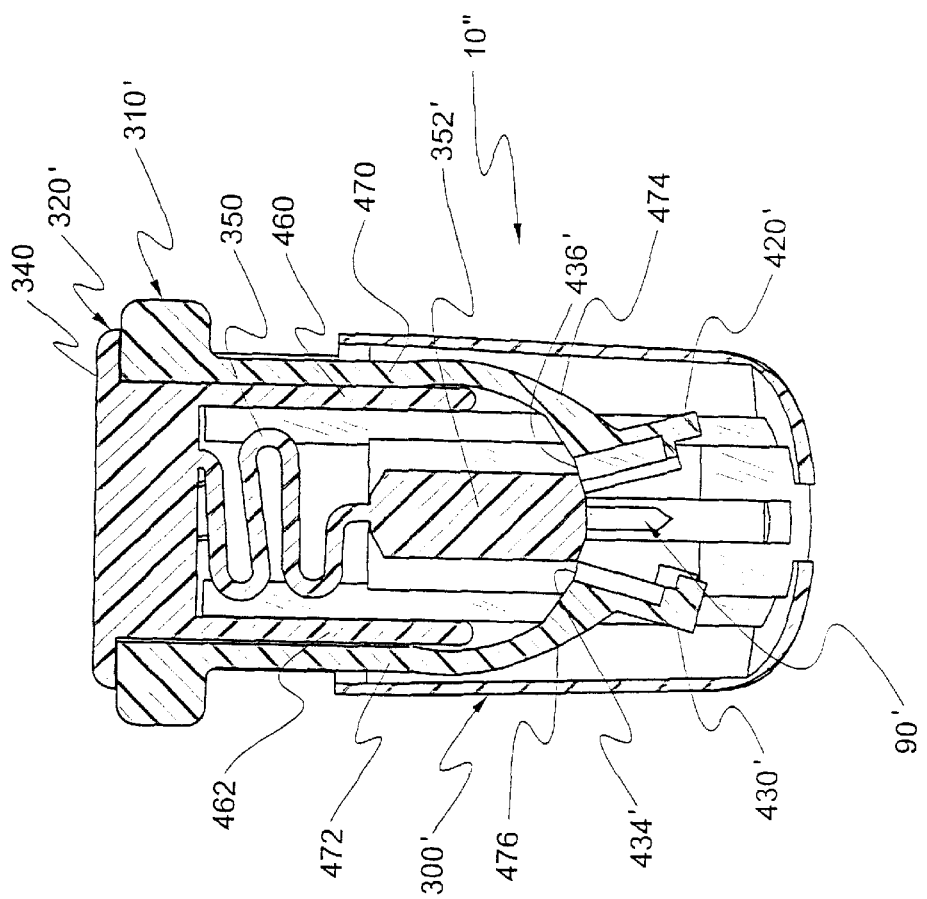
FIG. 26 is a cross section, similar to the cross section seen in FIG. 25, but with a spring portion compressed preparatory to firing the lancet.

In this description, the term proximal is generally used to indicate relative nearness of a referenced item to a user of a device or, when specified, to a viewer of a perspective drawing of a figure. The term distal is similarly used to indicate relative remoteness in both cases. The term assembly is used to represent a part of a device. The term subassembly is used to represent a part of an assembly. Reference is now made to the embodiments illustrated in FIGS. 1–26 wherein like numerals are used to designate like parts throughout. Parts which are similar in function, but different in form are designated by like numerals with primes being used to show differentiation of form. FIGS. 1–13 are views of elements of a first embodiment of the instant invention while FIGS. 14–24 depict elements of a second embodiment of the instant invention. FIGS. 25–26 depict a third embodiment.

Figure 1:
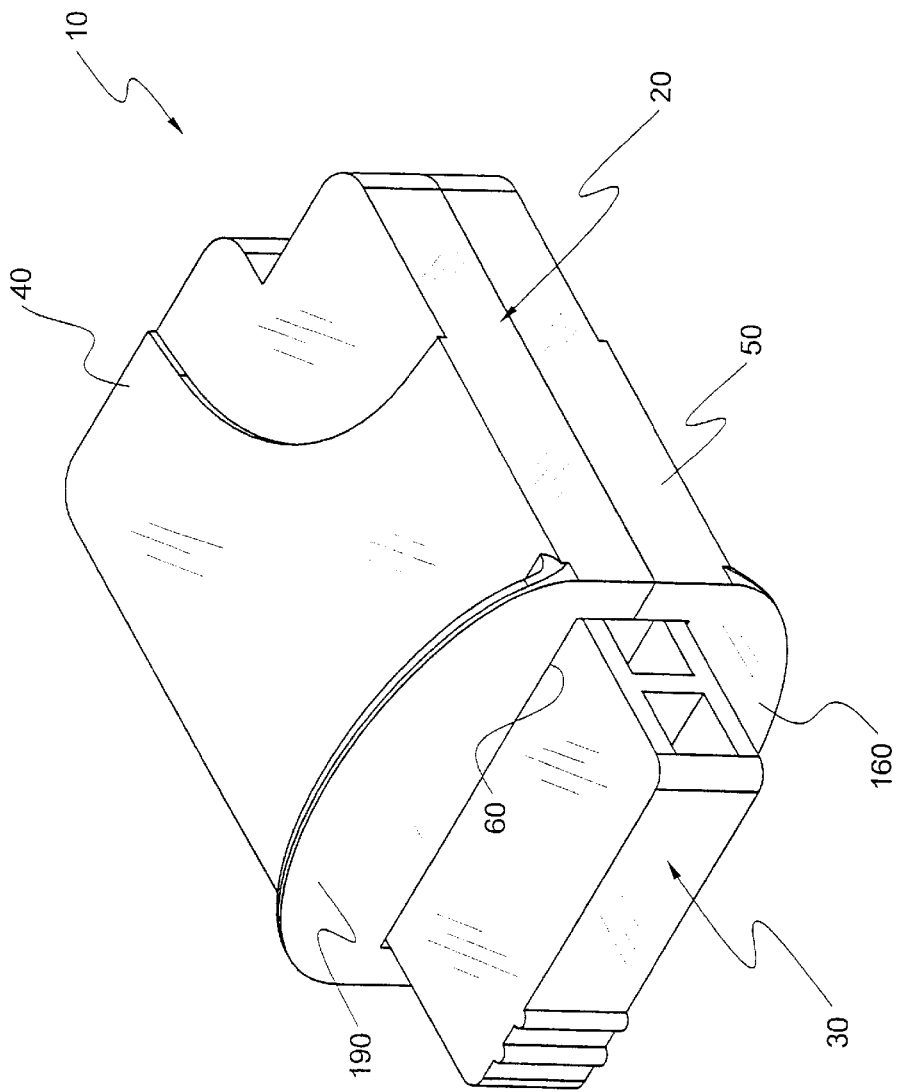
FIG. 1 is a perspective of a first embodiment of a single step lancet made according to the instant invention wherein an actuator and housing are seen to be disposed in a condition ready for use.
Figure 2:
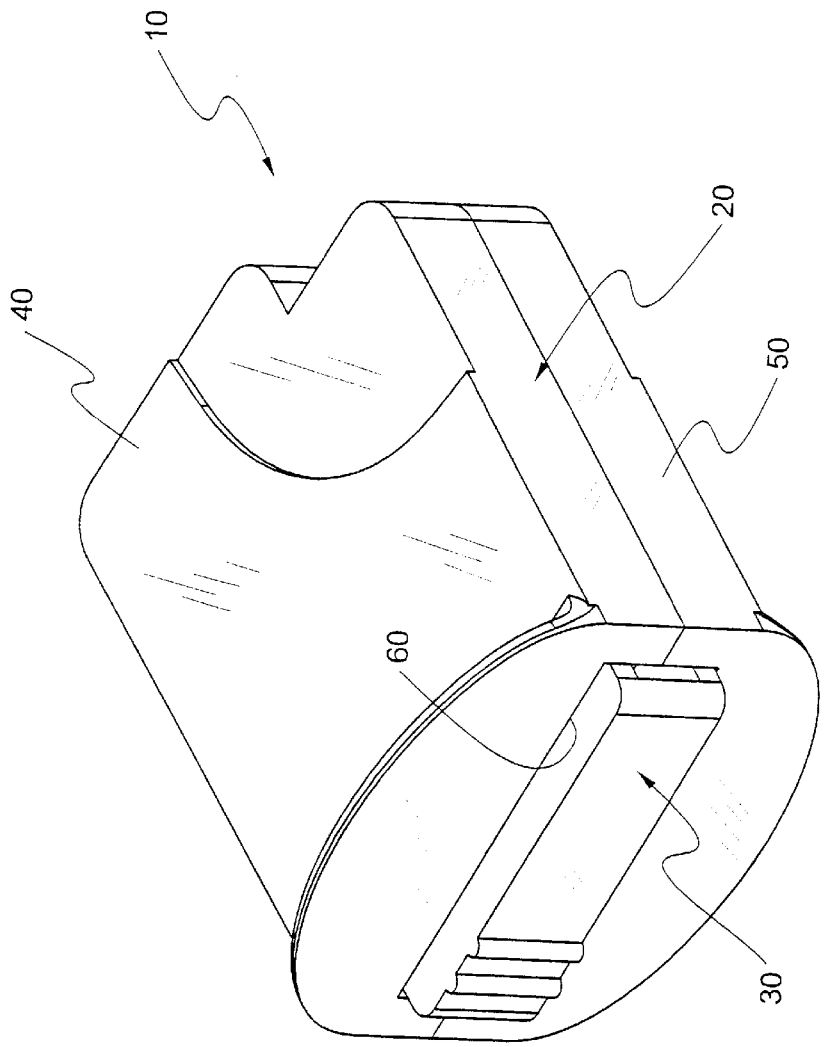
FIG. 2 is a perspective of the single step lancet seen in FIG. 1, but after firing the lancet by depressing the actuator into the housing.

As seen in FIG. 1, a self-contained lancet 10 comprises a housing 20 and an actuator 30. For ease of fabrication, housing 20 is formed by a cover portion 40 and a bottom portion 50. In combination, cover portion 40 and bottom portion 50 form a rectangular slot 60 through which actuator 30 is displaced to activate self-contained lancet 10. Consistent with the instant invention, lancet 10 requires no additional external packaging or other material which must be removed prior to use. Lancet 10 is activated by simply displacing actuator 30 into housing 20 as seen in FIG. 2.

Figure 3:
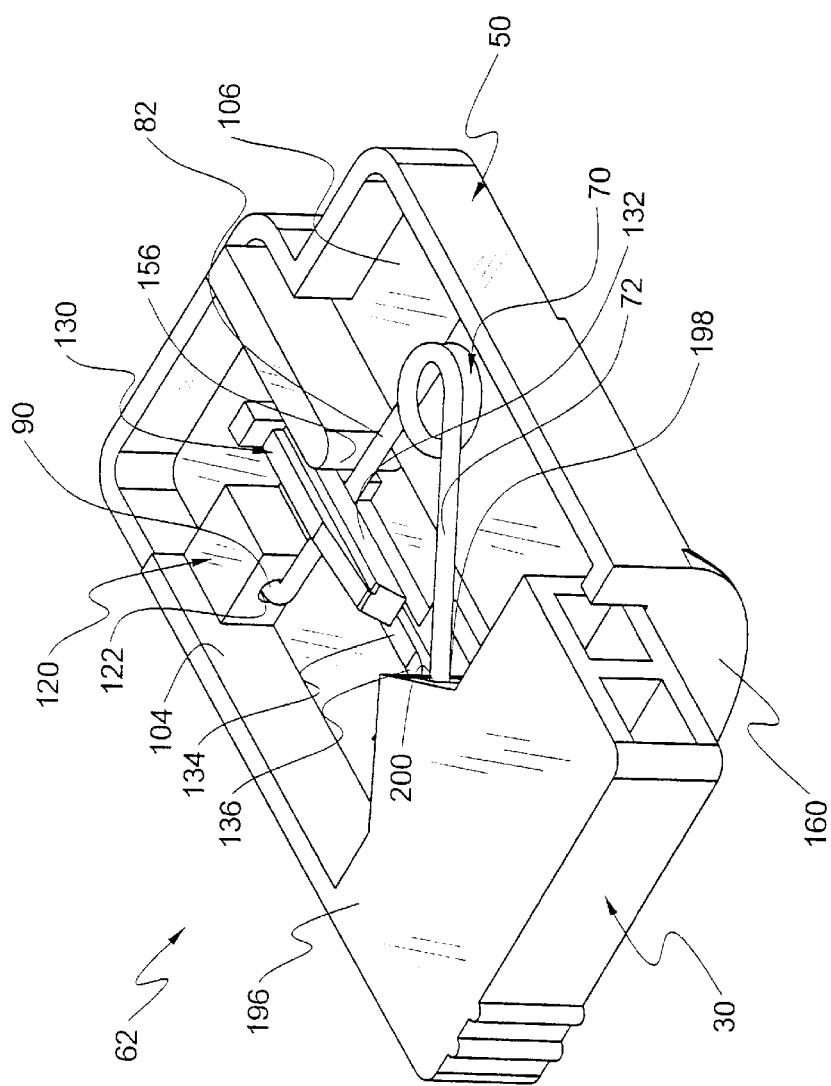
FIG. 3 is a perspective of the first embodiment of the single step lancet seen in FIG. 1 with a superior portion of the housing removed to permit parts internal to the lancet to be seen.

In FIG. 3, cover portion 40 is removed so that details of bottom portion 50 and otherwise hidden parts of lancet 10 may be seen in an uncovered device, referenced as number 62. Disposed in bottom portion 50 is a wire frame member 70. Wire frame member 70, better seen in FIG. 13, comprises an extended proximal leg 72, a medial section 74, and a distal end portion 76. Proximal arm 72 is substantially straight, ending abruptly at proximal end 78. Medial section 74 is wound into a helix to make a coil spring 80. Member 70 extends distally from coil spring 80 to define portion 76 comprising a distal leg 82 which ends at an abrupt bend 84 where a distal segment 86 is sharpened to provide a lancet blade 90.

Figure 11:
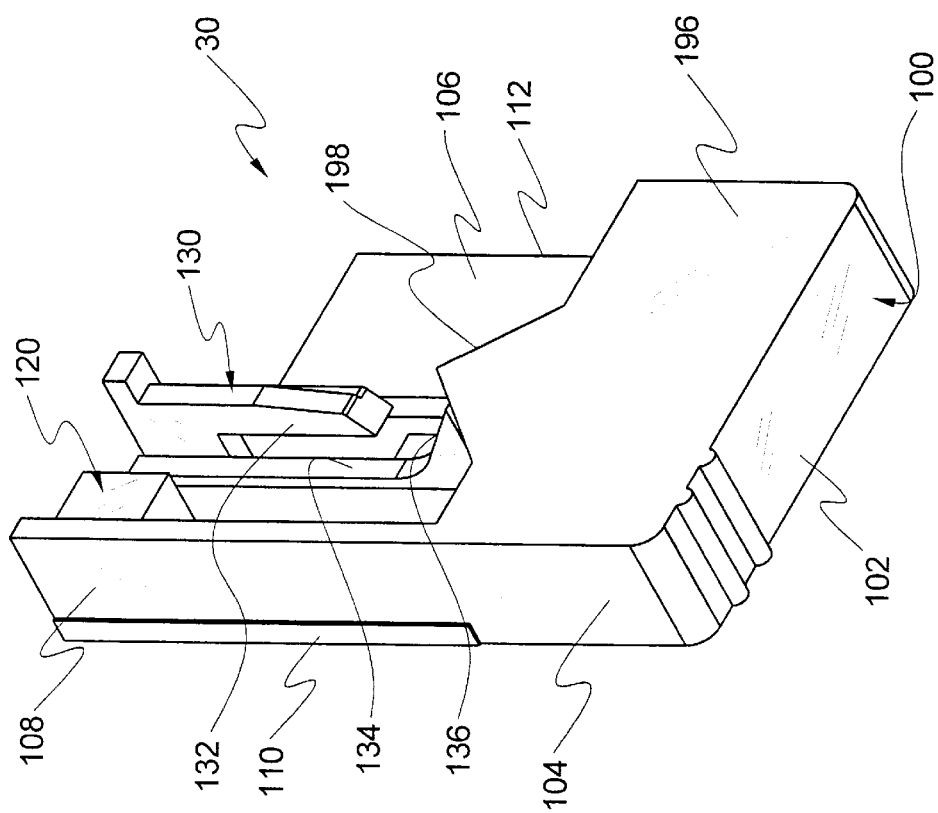
FIG. 11 is a perspective of the actuator.

Actuator 30 is seen as a separate part in FIG. 11 to comprise a proximally disposed digital interface 100. Digital interface 100 provides a substantially planar proximal surface 102 whereupon a thumb or finger may thrust actuator 30 inward into housing 20 to activate lancet 10. Contiguous with interface 100 is a first extended side member 104 which is vertically associated with a base plate 106 which is orthogonal to surface 102 and side member 104 in an inferiorly disposed plane.

On an external side 108, member 104 has an extended length side rail 110 which has substantially the same thickness as base plate 106. Rail 110 is used to provide a linear sliding surface between cover portion 40 and bottom portion 50 of housing 20. Similarly, on an opposite side 112, base plate 106 provides a function similar to that of rail 110.

A lancet blade retention and protection block 120 is medially disposed relative to adjacent member 104. As seen in FIG. 3, block 120 has a proximally disposed opening 122 wherethrough lancet blade 90 is inserted to provide antiseptic containment until lancet blade 90 is removed during a lancing procedure. As an example, opening 122 may be totally filled with lancet blade 90 and a material from which blade 90 may be easily extracted but which maintains a sterile environment for blade 90. Such a material may be silicone rubber.

Medially disposed upon base plate 106 is a guide assembly 130. In a plane, parallel to base plate 106 at the level of opening 122, guide assembly 130 provides a superiorly disposed restrainment 132 and an adjacent inferiorly disposed track 134 wherebetween a spacing is sized for containment and facile slideable travel of leg 82 of wire frame member 70. Adjacent track 134 has a sloped proximal incline 136, the purpose of which is disclosed in detail hereafter.

Figure 10:
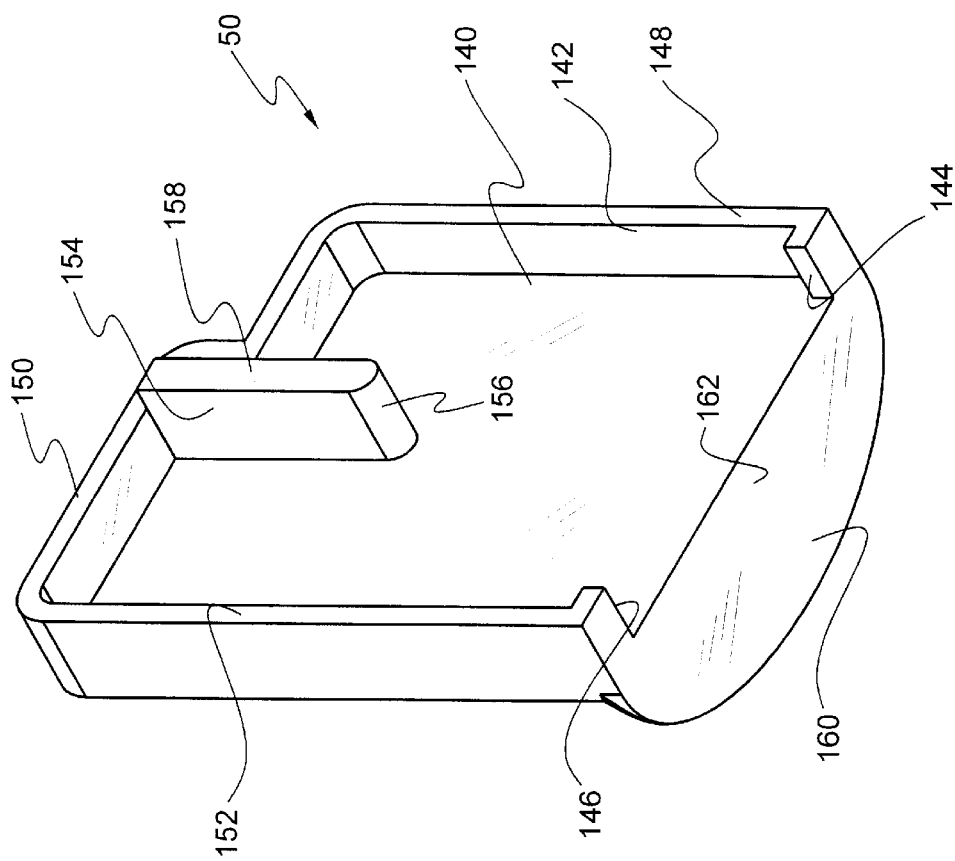
FIG. 10 is a perspective of the bottom or inferior portion of the housing.

Reference is now made to FIG. 10 wherein bottom portion 50 of lancet 10 is seen. Bottom portion 50 has a planar, solid cover 140 surrounded on three sides by a raised wall 142. Raised wall 142 ends abruptly at proximal edges 144 and 146 to provide a pathway through which actuator 30 is inserted. Raised wall 142, in a contiguous manner, continues from edge 144 to form a side wall 148, a distal wall 150 and another side wall 152. An elongated leg 82 displacement part 154 extends proximally from distal wall 150. Part 154 has a leg 82 (see FIG. 4) abutting face 156 which extends from the plane of cover 140 to a planar top surface 158. An inferiorly distending wing 160 may be noted, as extending orthogonally from a proximal edge 162 of cover 140.

Figure 12:
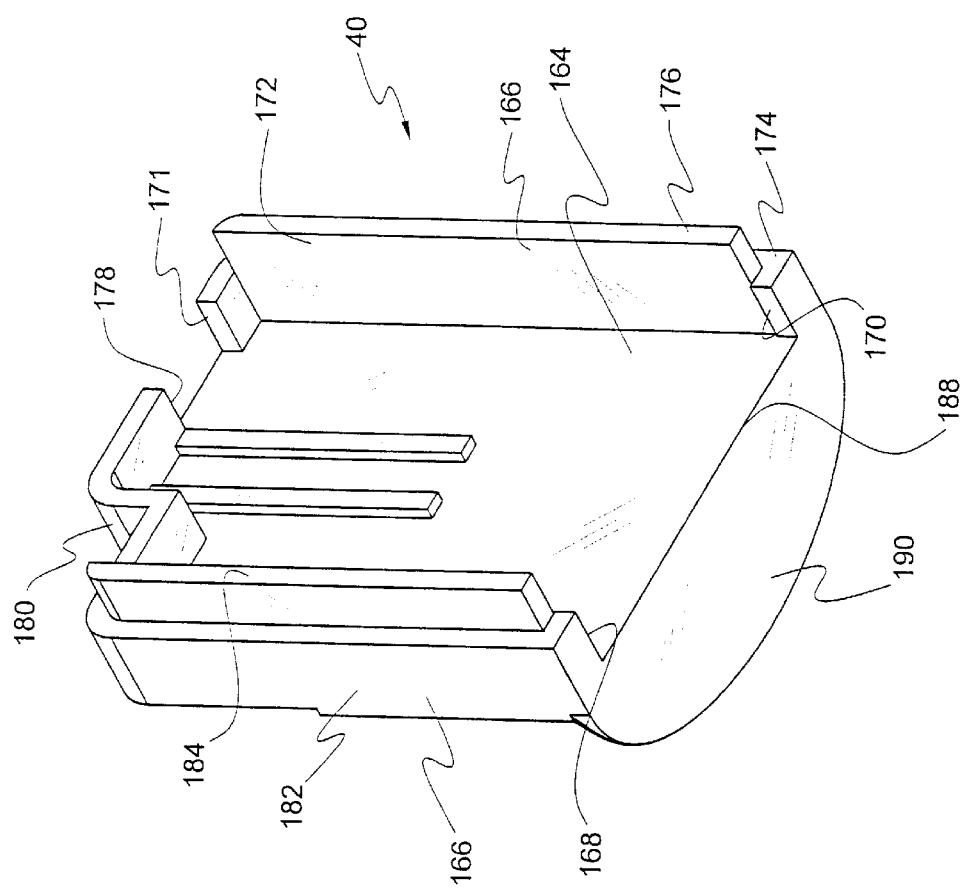
FIG. 12 is a perspective of the superior or covering portion of the housing.
Figure 13:
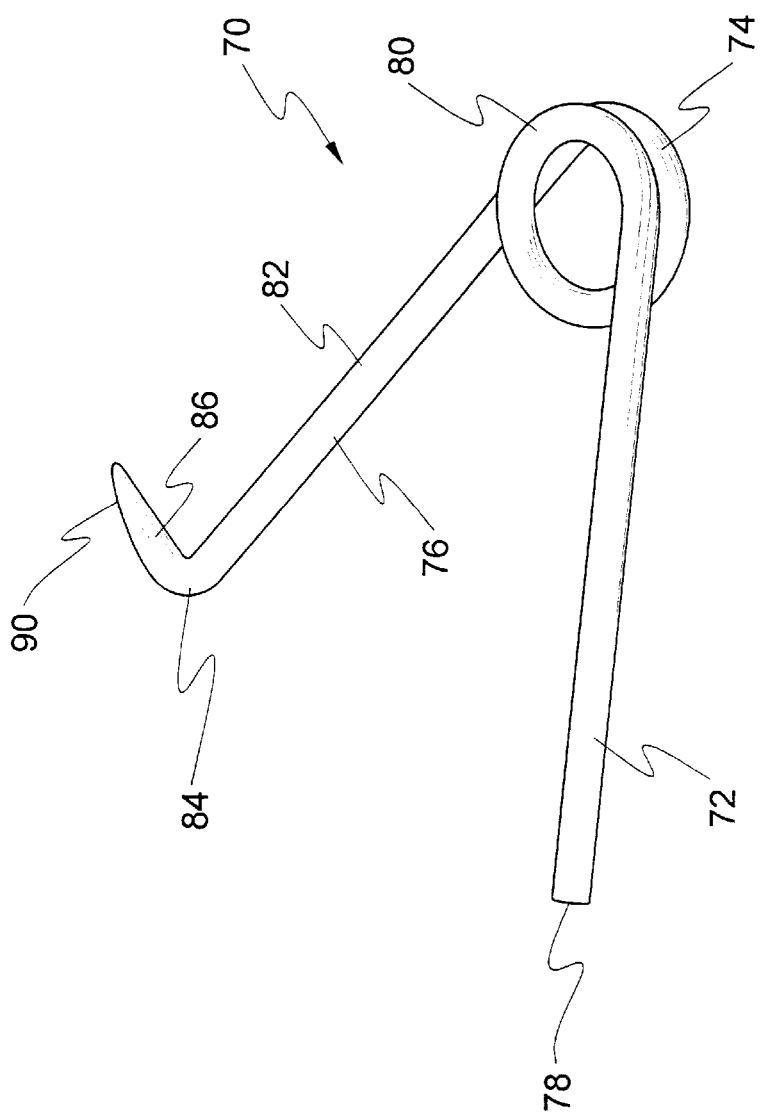
FIG. 13 is a perspective of the spring and lancet blade combination.

A mating cover, previously referenced in FIG. 1 as superiorly disposed cover portion 40, affixed to cover portion 50 is seen in FIG. 12. Similar to cover portion 50, cover portion 40 has a planar, solid cover 164. Also similar to cover portion 50, cover portion 40, with a single exception, is substantially surrounded on three sides by a raised wall, generally designated 166. As is the case of wall 142, wall 166 ends abruptly at proximal edges 168 and 170, thereby providing a portion of the pathway for actuator 30 insertion. Wall 166 extends distally from edge 170 to another abrupt edge 171 to form a raised wall 172 having an exterior ledge 174 which is inferior to an interior ledge 176.

Juxtaposed edge 171 is a second abrupt edge 178. In combination, edges 171 and 178, cover plane 164 and raised wall 142 (see FIG. 10) are sized and separated to form a slot through which lancet blade 90 passes during a lancing procedure. From edge 178 to edge 168, raised wall 166 is contiguously defined by a distal wall section 180 and a side wall 182 having an exterior ledge 184 which is inferior to an interior ledge 186. Ledges 174 and 184 and distal wall section 180 are sized and spaced to juxtapose and join against raised wall 142 when cover 40 is disposed in contact with cover 50 to form housing 20 of lancet 10. Extending orthogonally away from planar cover 164 at a proximally disposed communicating line 188 is a second distending wing 190. In combination wings 160 and 190 combine to form finger handles for fingers or the like used to grasp and hold lancet 10 while actuator 30 is depressed into housing 20.

Ledges 176 and 186 are sized and spaced apart to provide medially disposed slideable contact with raised wall 142 of bottom 50. Further ledges 174 and 184 contact superior edges of raised wall 142 to define thickness of lancet 10. When cover portion 40 is joined with cover portion 50, ledge 176 acts as a vertically constraining guide for side rail 110 of actuator 30 while ledge 184 acts similarly as a constraining guide at side 112 (see FIG. 11) to thereby assure linear displacement of actuator 30 relative to housing 20. Distending medially from distal wall 180, are a pair of raised rails 192 and 194 which are disposed to fit about part 154 of cover portion 50 to further stabilize lancet 10 when assembled with cover portion 40 to form housing 20.

Referring again to FIG. 11, digital interface 100 further has a distal segment 196 which has an angled distal face 198. Distal face 198 has a medially disposed anchor hole 200 (seen in FIG. 3) sized to receive and anchor end 78 (see FIG. 13) of leg 72 of wire frame member 70.

To assemble lancet 10 for use, wire frame member 70 is displaced into actuator 30, as seen in FIG. 3, such that elongated leg 82 is disposed in guide assembly 130 which provides superiorly disposed restrainment 132 and adjacent inferiorly disposed track 134. Proximal end 78 (seen in FIG. 13) is displaced into anchor hole 200. So disposed, wire frame member 70 is preferably in a relaxed state, although slight tension may be employed within the scope of the invention. Actuator 30 with wire frame member 70 in place is displaced into cover portion 50, as seen in FIG. 3. Releasible detents (not shown) may be used to temporarily hold actuator 30 in place as disposed in FIG. 3. Use of such detents is well known in the state of lancet design art. Finally, cover portion 40 is affixed to cover portion 50 to form a complete lancet 10, as seen in FIG. 1.

Figure 4:
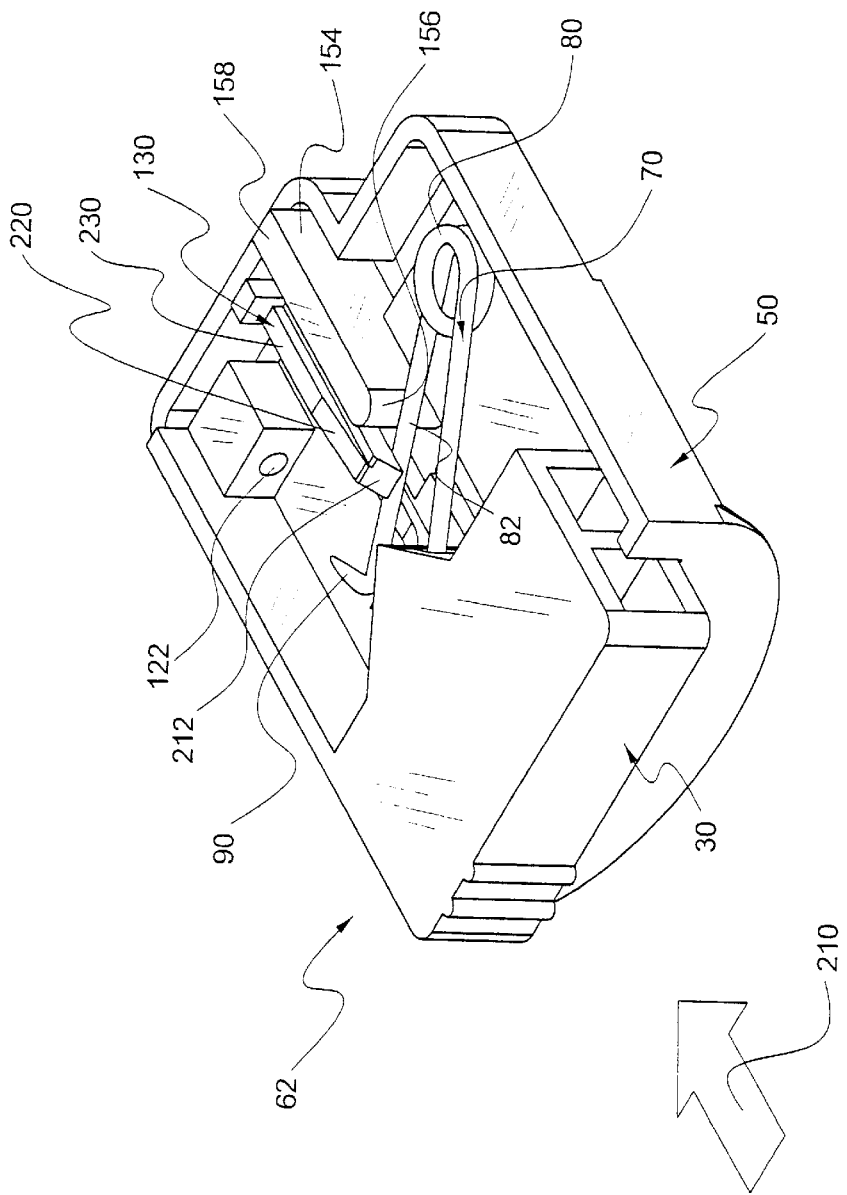
FIG. 4 is a perspective, similar to the perspective of FIG. 3, but with the actuator partially depressed in a lancet firing cycle.

Reference is now made to FIGS. 4–9 where lancet 10, seen, as in FIG. 3, with cover portion 40 removed. Initiation of a lancing cycle is seen in FIG. 4, wherein actuator 30 is displaced in direction of arrow 210 into cover portion 50. Leg 82 abutting face 156 of part 154 inhibits distal travel of leg 82 of wire frame member 70 storing energy in coil spring 80. Note that lancet blade 90 has been displaced from opening 122 and that no further contact with lancet blade 90 occurs during the lancing cycle.

Figure 5:
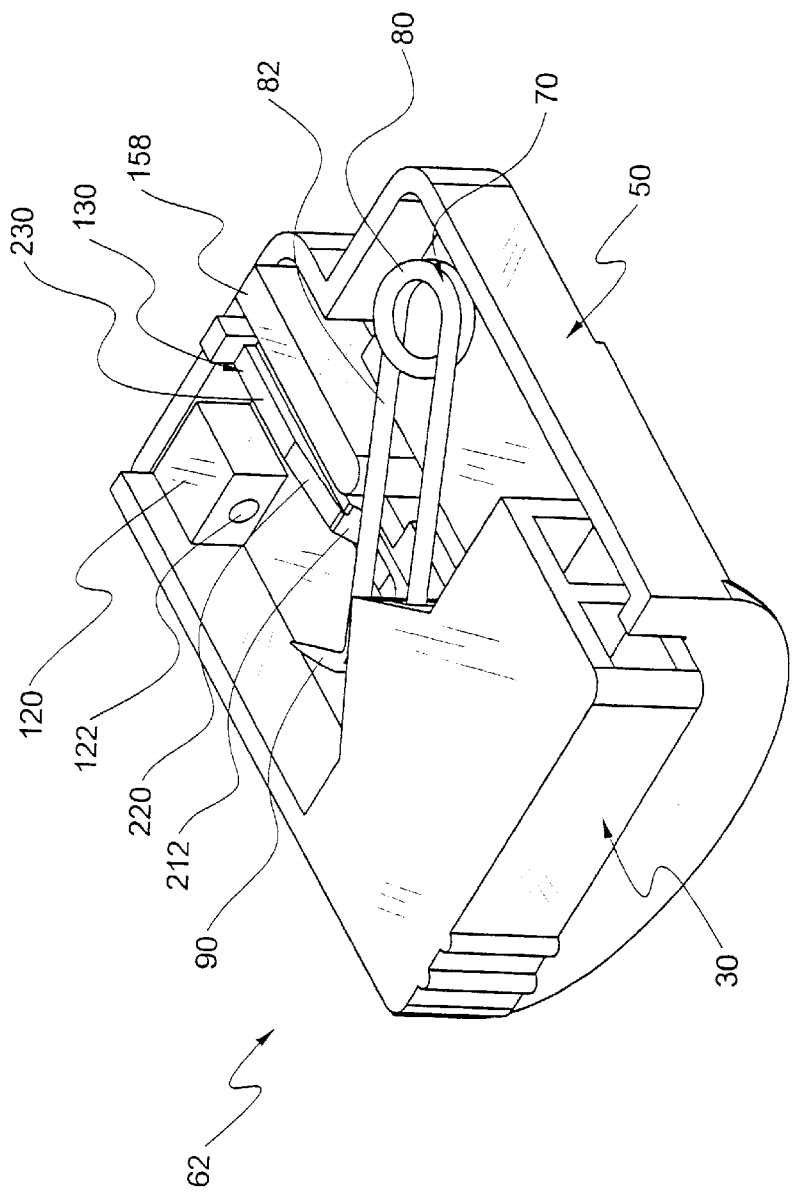
FIG. 5 is a perspective, similar to the perspective of FIG. 4, but having the actuator further depressed thereby showing a continuation of the lancet firing cycle.
Figure 6:
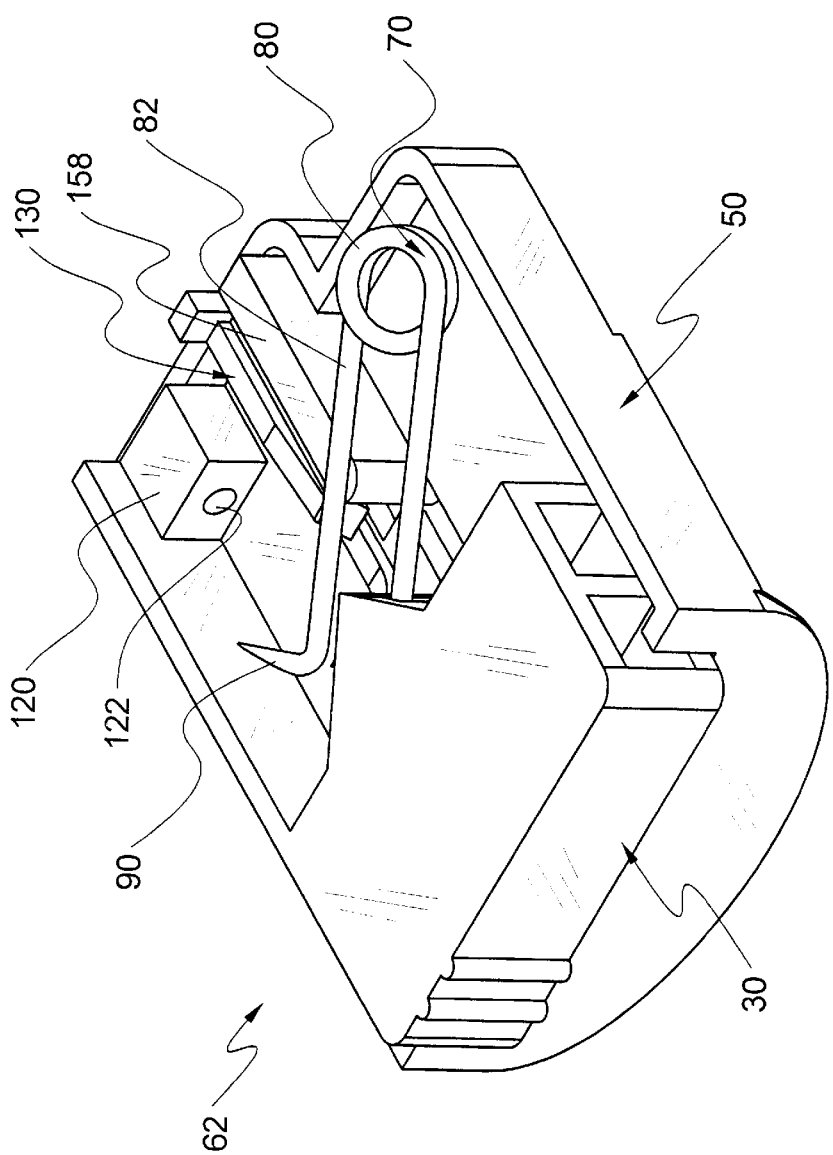
FIG. 6 is a perspective, similar to the perspective of FIG. 5, completing depression of the actuator into the housing with resulting action begun by a spring and lancet blade combination.
Figure 7:
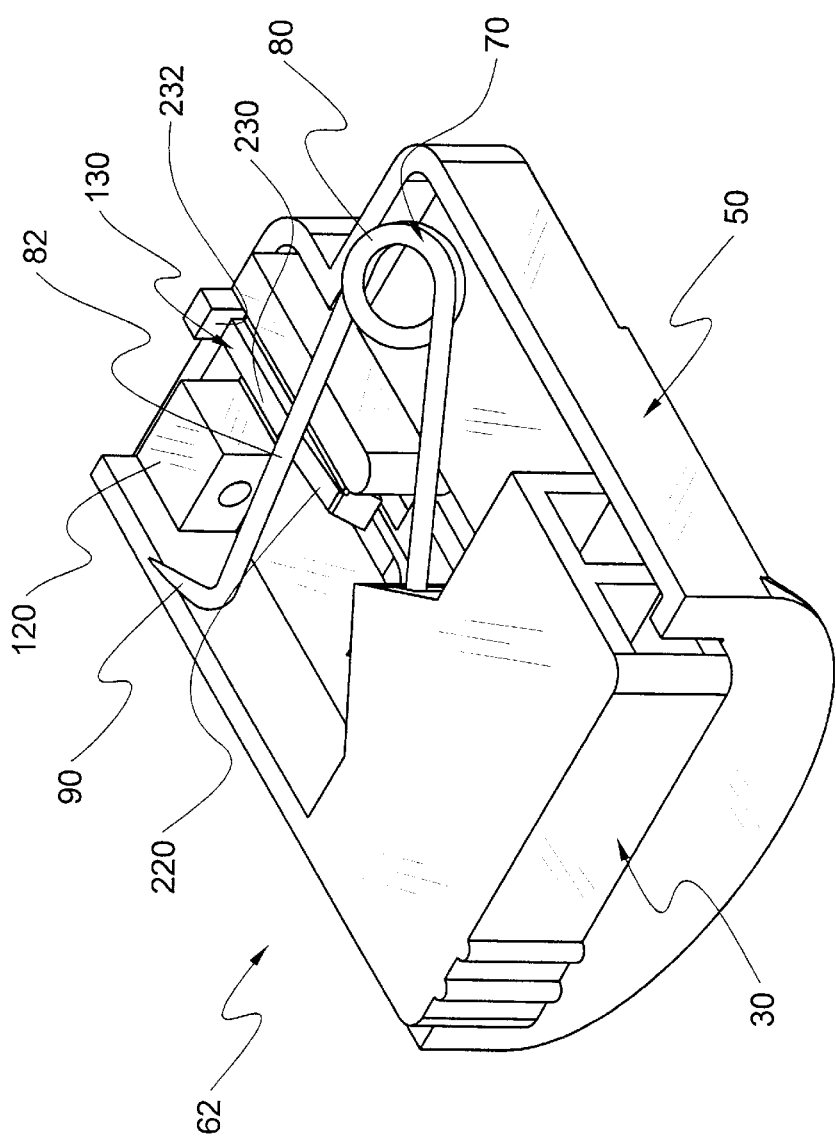
FIG. 7 is a perspective, similar to the perspective of FIG. 6, wherein advancing of the lancet blade under force of the spring is seen.
Figure 8:
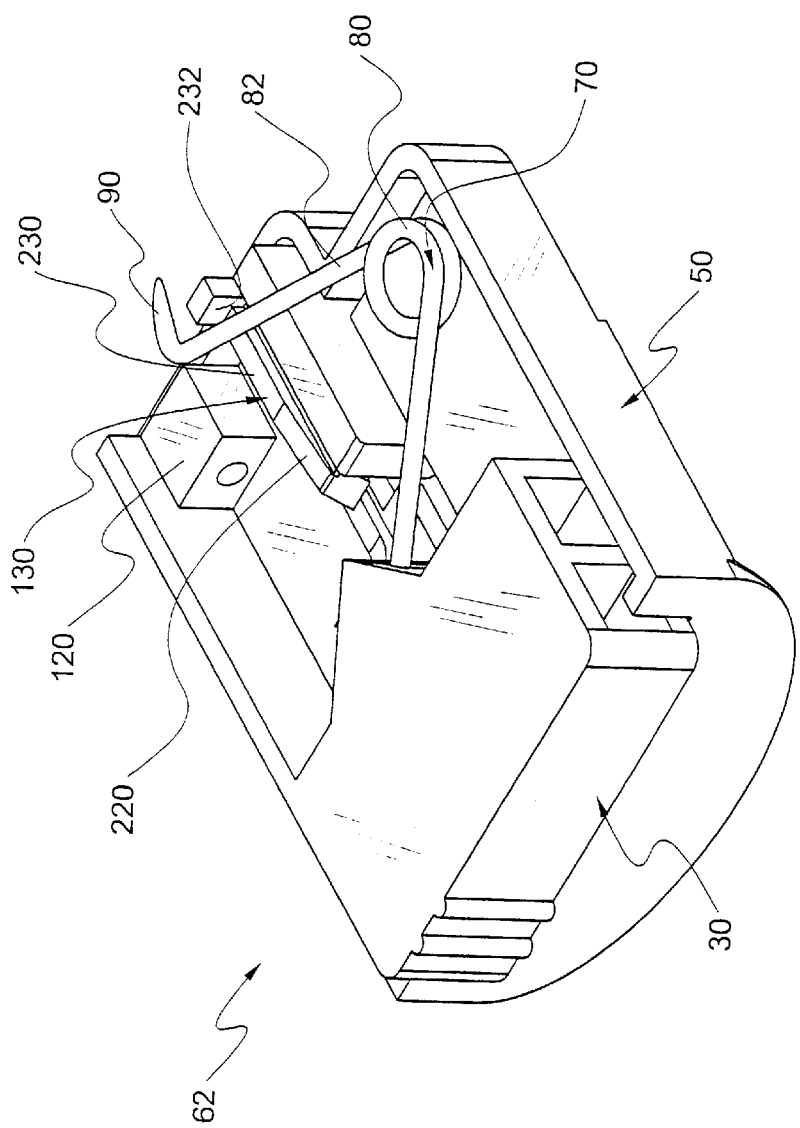
FIG. 8 is a perspective, similar to the perspective of FIG. 7, wherein over travel of the spring causes the lancet blade to be displaced outside of the housing.
Figure 9:
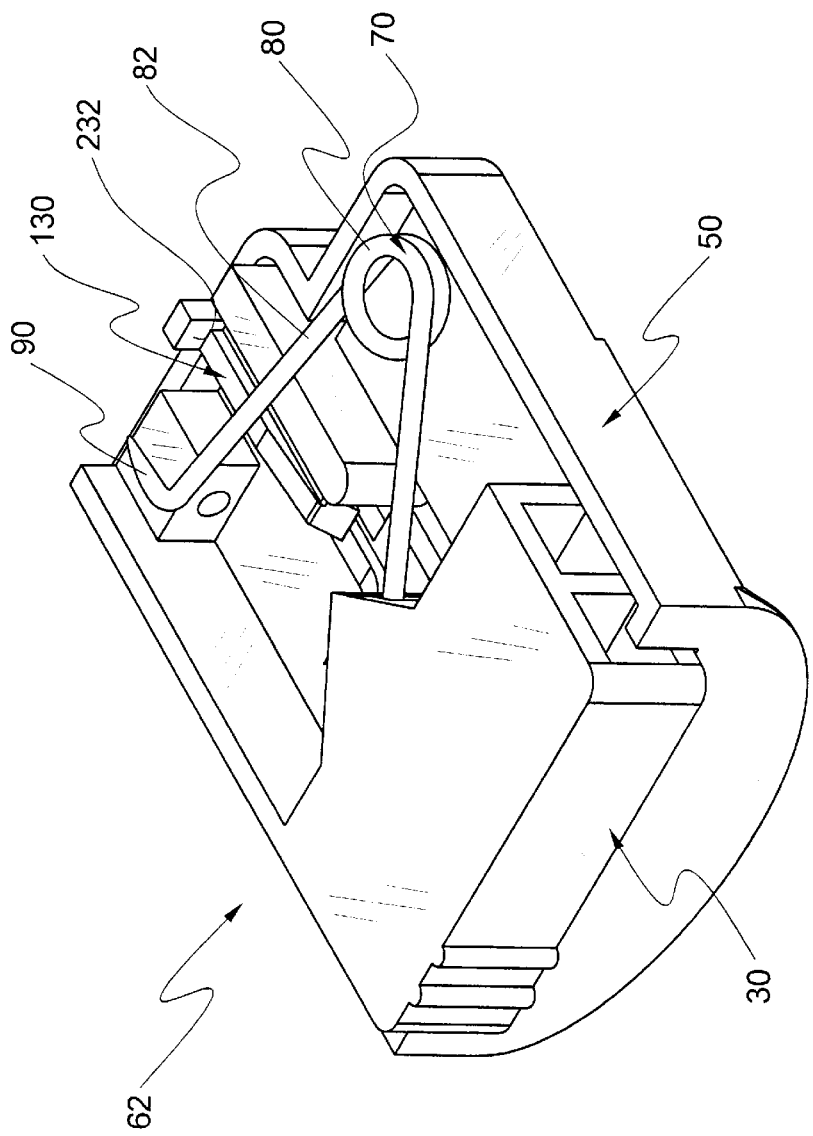
FIG. 9 is a perspective, similar to the perspective of FIG. 8, wherein the final contraction of the spring to a rest state retracts the lancet blade to a safety position within surroundings of the housing.

Continuing inward displacement of actuator 30 into cover portion 50 results in upward displacement of leg 82 as seen in FIG. 5, the upward displacement being caused by contact between leg 82 and proximal incline 136 (see FIG. 3). Note that guide assembly 130 has a proximally disposed upwardly sloped surface 212 which is contiguous with another surface 220 of a lesser upward slope which continues distally with a substantially level surface 230. In combination, surfaces 210 and 220 urges distally progressing leg 82 to a plane which effectively guides blade 90 above block 120 and through the slot formed by edges 178 and 171 and cover plane 164 (see FIG. 12) through which lancet blade 90 passes during a lancing procedure, as earlier disclosed. In FIG. 6, leg 82 is freed to travel distally over planar top surface 158. In FIG. 7, leg 82 reaches the distal end of surface 220. In FIG. 8, lancet blade 90 extends away from the slot delineated by edges 171 and 178. Note also, a block 232, disposed at the distal end of surface 220, which impedes further travel of blade 90 (via leg 82) to determine depth of penetration of blade 90. In FIG. 9, spring action of coil 80 returns lancet blade 90 into protective safety of cover 50 (and cover 40, not shown).

Note that the only action required to displace lancet blade 90 from a protected environment to a lancing and then safety protected position is the result of a single unidirectional depression of actuator 30 into the covers 40 and 50. There are no disposable parts other than the spent lancet 10 itself. Except for lancet blade 90, all parts of lancet 10 are preferably made from synthetic resinous parts, such as injection molded polypropylene.

Figure 14:
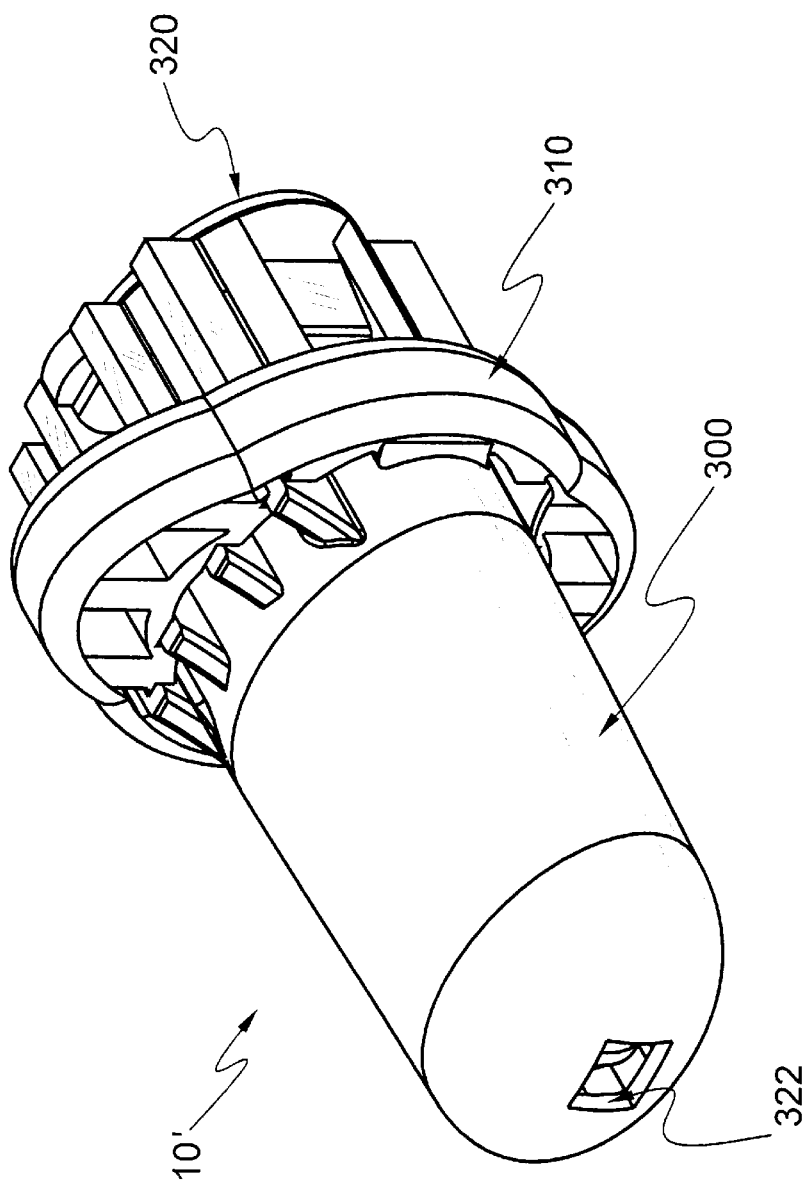
FIG. 14 is a perspective of a second embodiment of a single step lancet made according to the invention wherein portions of a housing, a ring/blade shield assembly and an actuator and blade assembly are seen to be disposed in a condition ready for use.
Figure 15:
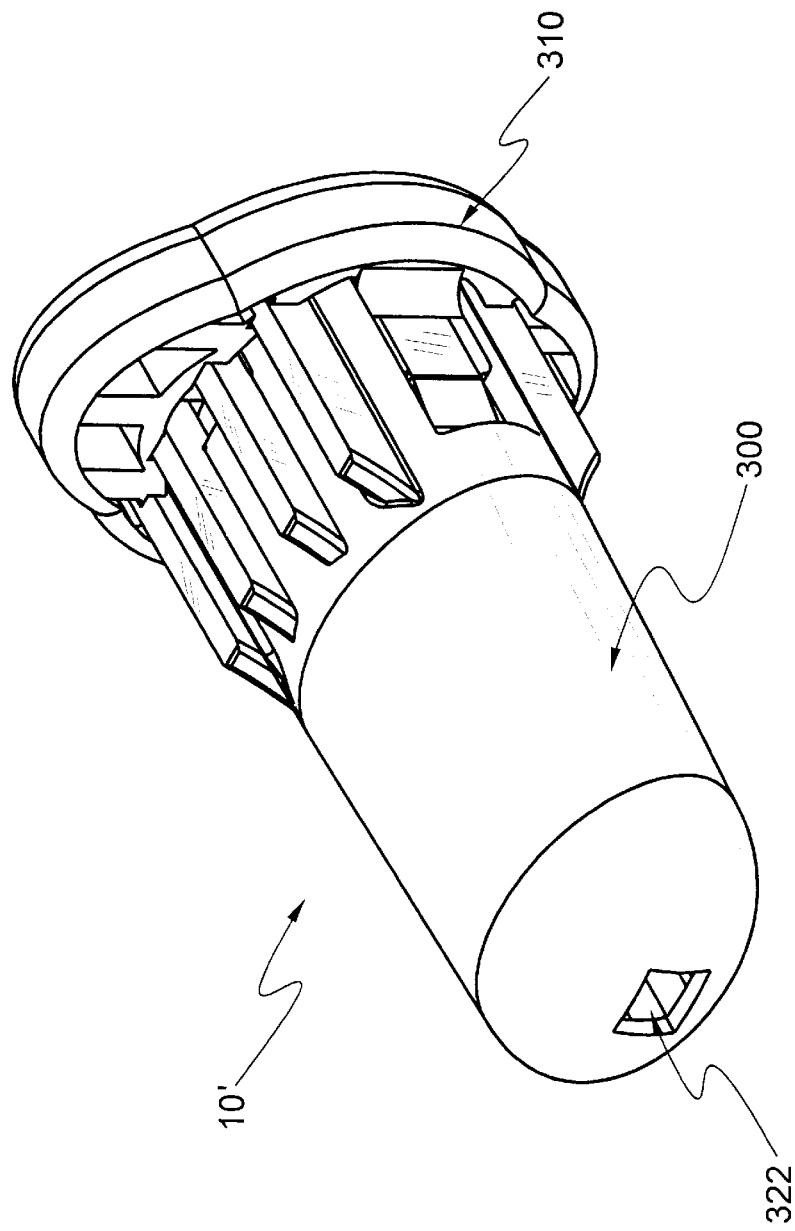
FIG. 15 is a perspective of the embodiment of FIG. 14 after firing of the lancet.

Reference is now made to FIGS. 14–24 wherein parts and assemblies of another embodiment of a lancet 10' according to the present invention is seen. As seen in FIG. 14, lancet 10' is assembled from three injection molded parts, a housing 300, a ring/blade shield assembly 310 and an actuator and blade assembly 320. In the state seen in FIG. 14, lancet 10' is ready to activate. To activate lancet 10', ring/blade shield assembly 310 is drawn proximally about actuator and blade assembly 320 and portions of housing 300 causing a lancet blade 90' (which may be seen in FIGS. 17–20, 23 and 24) ultimately to be displaced outward from a distal slot or orifice (which is referenced as 322) in housing 300 to perform a lancing function and then to be returned, for safety, into housing 300, as seen in FIG. 15. Note that actuator and blade assembly 320 is largely hidden from view by housing 300 and ring/blade shield assembly 310 in FIG. 15.

Figure 16:
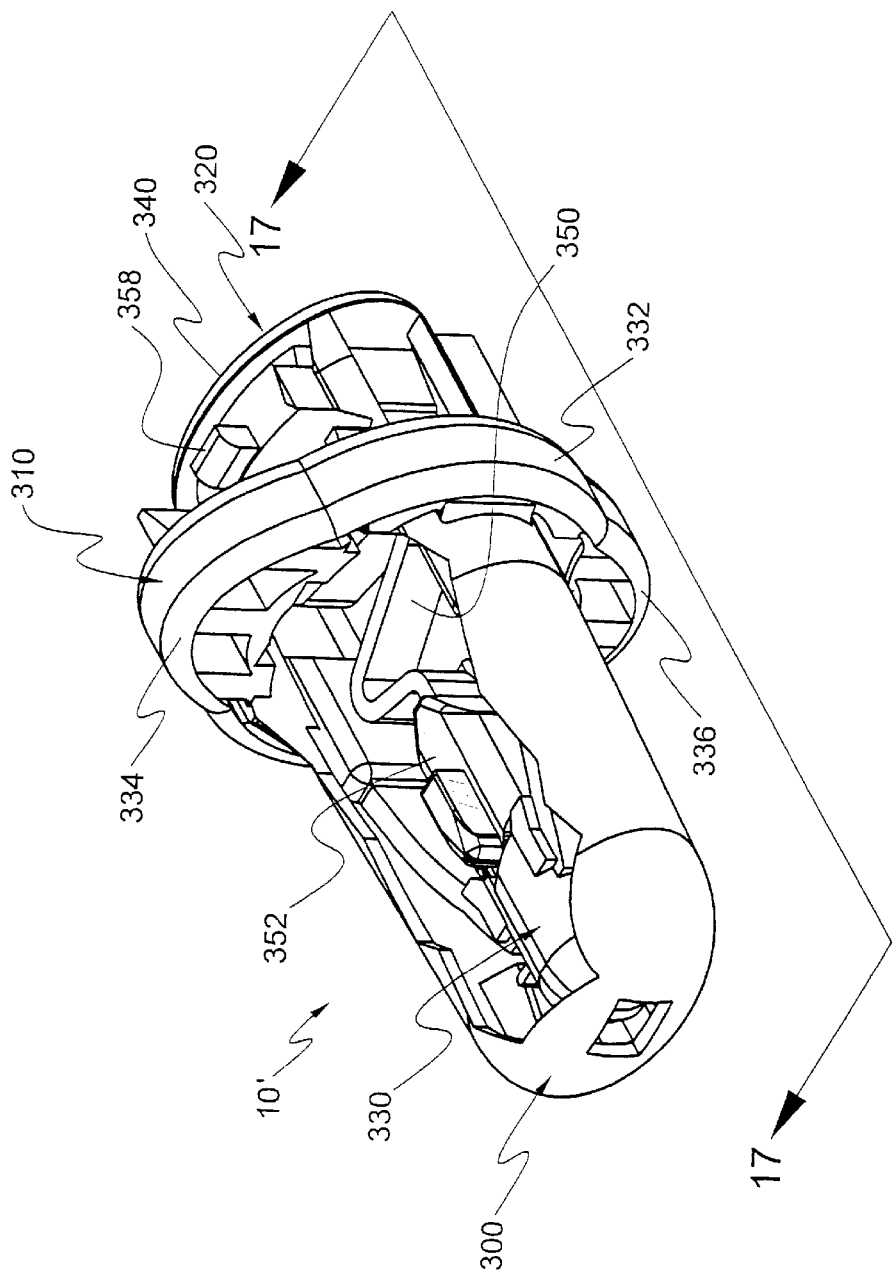
FIG. 16 is a perspective of the embodiment of FIG. 14 with a portion of the housing cut away to permit viewing of parts disposed therein.

A portion of housing 300 is cut away in FIG. 16 to reveal greater detail of ring/blade shield assembly 310 and actuator and blade assembly 320. Distally, ring/blade shield assembly 310 is seen to comprise a displaceable shield 330 for a lancet blade 90', hidden in FIG. 16. Ring/blade shield assembly 310 comprises a proximally disposed actuator ring 332 having juxtaposed outwardly extending wings 334 and 336 by which a proximally directed force is imposed upon ring/blade shield assembly 310 to displace assembly 310 proximally relative to housing 300 and actuator and blade assembly 320. A proximally disposed planar digitary actuator button 340 is disposed to provide a site for applying a force opposing the proximally disposing force imposed upon ring/blade shield assembly 310 to activate lancet 10'. A spring 350, which compressively stores energy as actuator button 340 and wings 334 and 336 are displaced toward one another interconnects actuator button 340 to blade 90' through a blade mounting hub 352.

Figure 23:
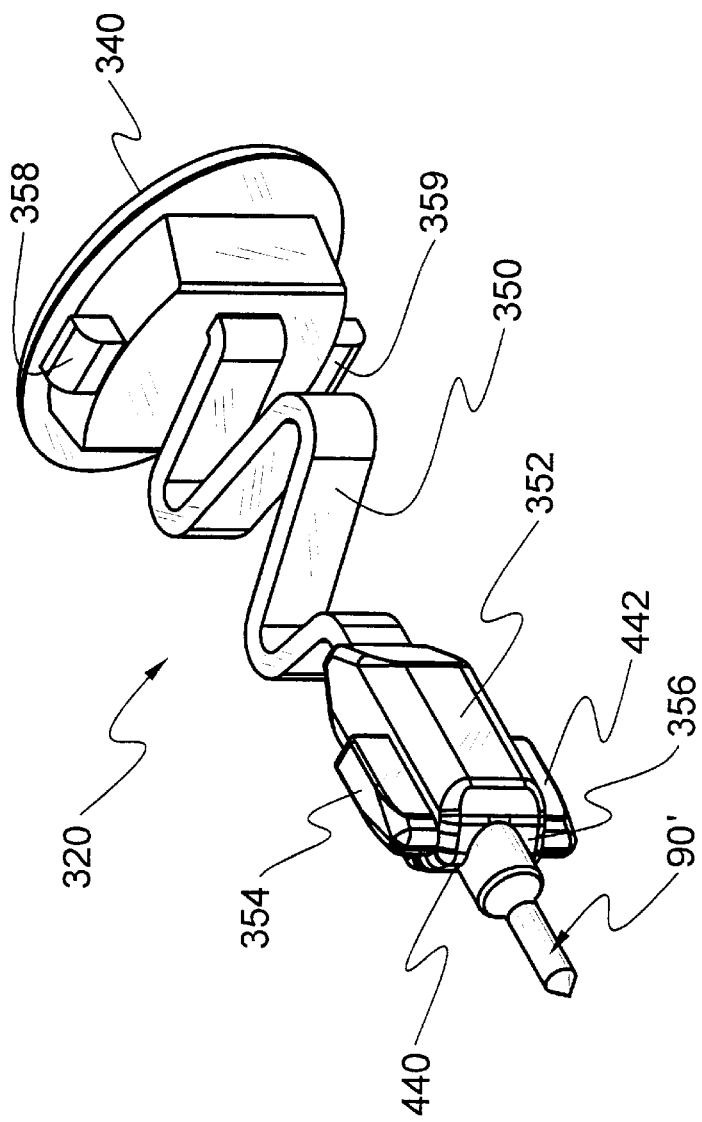
FIG. 23 is a perspective of the actuator and blade assembly, first seen in FIG. 14.

Reference is now made to FIG. 23 which shows actuator and blade assembly 320 as a single part. Preferably, by insert molding blade 90', into blade mounting hub 352, actuator and blade assembly 320 may be made as a single, straight pull injection molded part. Part 320 may be made from Delrine®, a Dupont Trademark, or a acetal resin (such as Tenac 4520 available from Asahi Chemical Industry Company, Ltd.) or any other material, e.g. synthetic resinous material which provide appropriate compressive spring deflection and retraction characteristics. Of course, in a more costly embodiment, a metal spring may be used within the scope of the invention.

Hub 352 also comprises a pair of extended rectangular guide bars 354 and 356 employed to ride in guides molded into housing 300 to assure linear displacement of blade 90' during retraction and lancing. Proximally disposed in the same vertical plane as guide bars 354 and 356 are a pair of knobs 358 and 359 which are used to engage housing 300 and maintain actuator and blade assembly 320 and housing 300 in secure, closed association with ring/blade shield assembly 310 after lancet firing as a readily discernable tamper evidence and used part indicator and assure blade 90' remains covered for safety.

Figure 21:
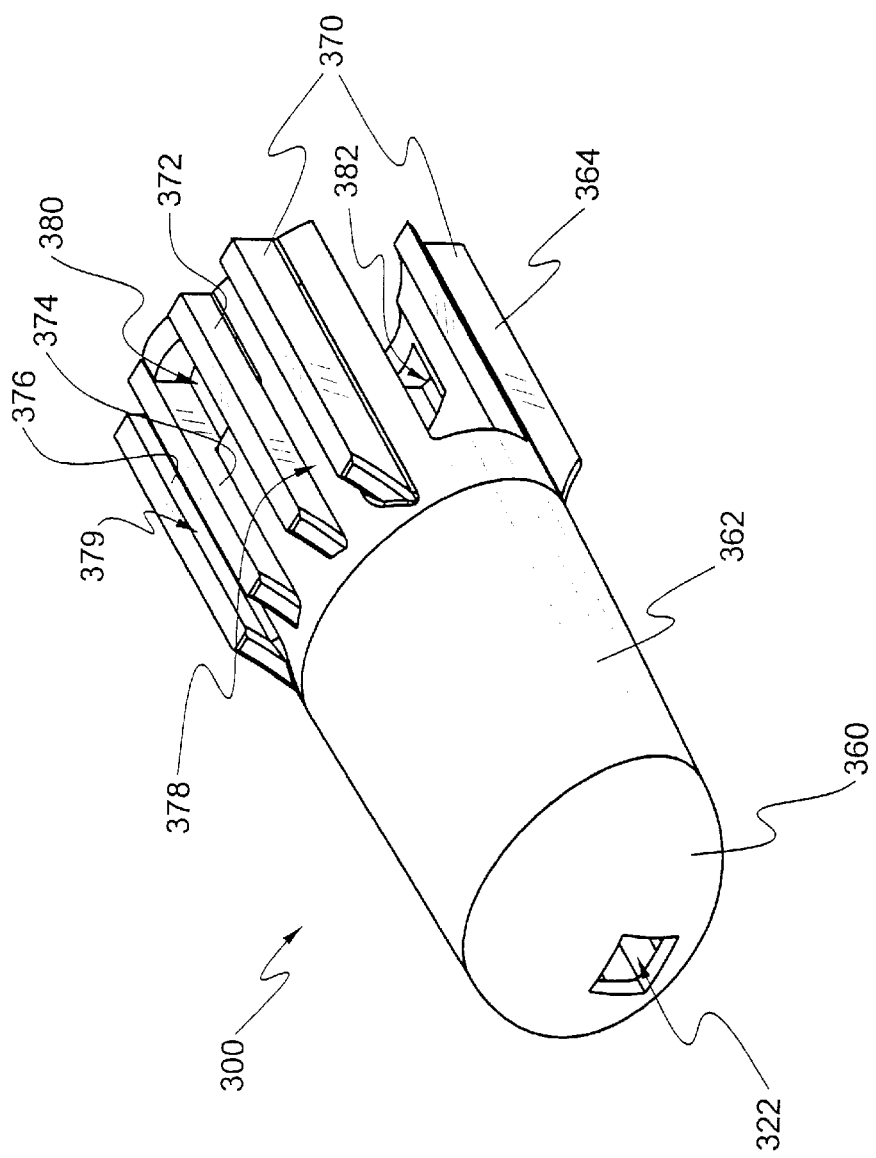
FIG. 21 is a perspective of the housing, first seen in FIG. 14.

Reference is now made to FIG. 21 wherein housing 300 is seen as a single part. As earlier mentioned, housing 300 comprises a distal slot or orifice 322 through which blade 90' passes during a lancing cycle. Distally away from orifice 322, housing 300 broadens through an asymmetrical elipsoidal member 360 to a body part 362.

Proximally from body part 362, housing 300 has a ribbed section 364. Four pairs of guide ribs (numbered 370, 372, 374 and 376) are disposed on inferior and superior sides of ribbed section 364. Each pair of ribs are juxtaposed on the inferior and superior sides of ribbed section 364 as exemplified by guide rib pair 370. Only one rib of each pair of guide ribs 372, 374 and 376 is seen in FIG. 21.

In combination ribs 370 and 372 form a guide groove 378. Likewise ribs 374 and 376 form a guide grove 379. Such grooves 378 and 379 are disposed on both superior and inferior sides of ribbed section 364. As well, ribbed section 364 comprises two proximally disposed catch slots 380 and 382 positioned to be in alignment with knobs 358 and 359, respectively (see FIG. 23). Note that when knobs 358 and 359 are disposed within slots 380 and 382 when actuator and blade assembly 320 is securely and unreleasibly affixed to housing 300, in the lancet 10' activated state seen in FIG. 15.

As seen in FIG. 21, housing 300 may be made from a single direction pull injection molded part. Housing 300 is preferably made from synthetic resinous material such as polypropylene or polyethelene.

Figure 22:
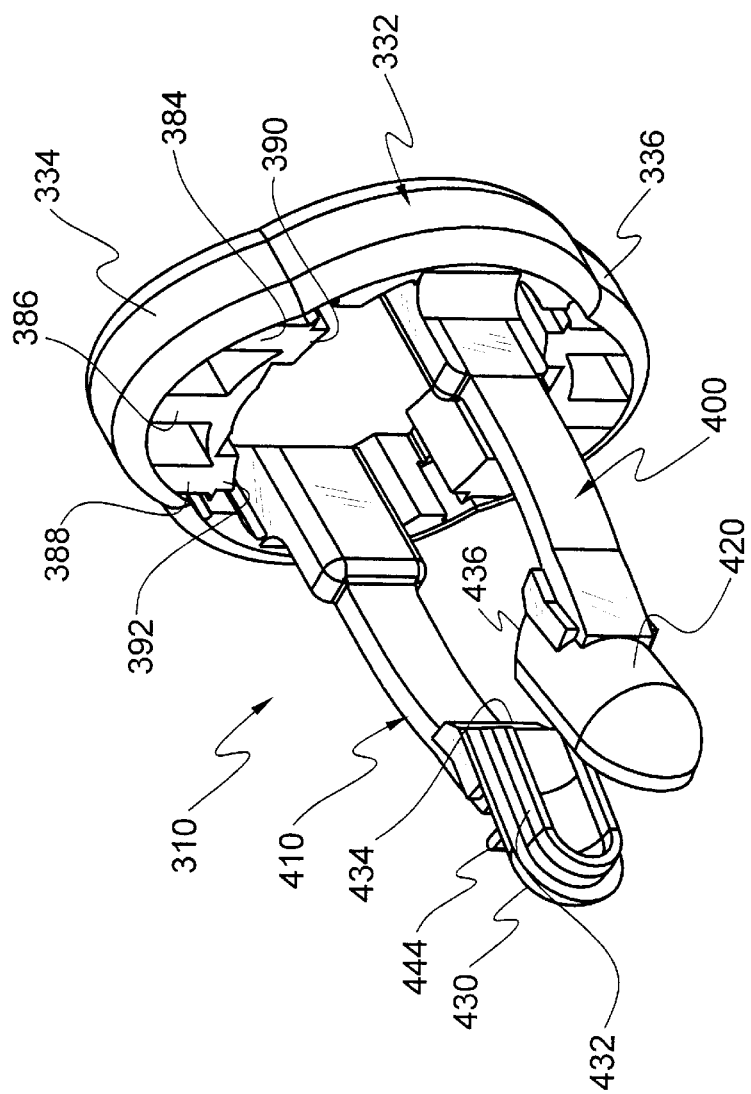
FIG. 22 is a perspective of the ring/blade shield assembly, first seen in FIG. 14.

Ring/blade shield assembly 310 is seen as a single part in FIG. 22. As disclosed earlier, ring/blade shield assembly 310 comprises proximally disposed actuator ring 332 having juxtaposed outwardly extending wings 334 and 336. Inferiorly disposed relative to wing 334 are three downwardly and inwardly extending ribs 384, 386 and 388. Note that rib 384 is inwardly bounded by a rectangularly shaped knob 390 which is sized and shaped to slide within a guide groove, such as guide groove 378, seen in FIG. 21. Similarly, rib 388 is inwardly bounded by a rectangularly shaped knob 392 which is similarly sized and shaped to slide within a guide groove, such as guide groove 379, also seen in FIG. 21. Likewise, similarly inwardly extending ribs (unnumbered) from wing 336 are sized and shaped to slide within inferiorly disposed guide grooves of housing 300.

Extending distally from actuator ring 332 are a pair of elongated legs, numbered 400 and 410. At the distal end of leg 400 is a blade shield part 420. Similarly, at the distal end of leg 410 is a blade shield part 430. In combination, parts 420 and 430 are designed as clamshells which enclose and provide side aseptic barriers which protect sides and distal end of blade 901 when parts 420 and 430 are disposed together about blade 90'. Note that part 430 has a raised sealing ring 432 which is sized and shaped to fit within a sealing shell (not shown in FIG. 22) disposed in an opposing face of part 420. When disposed together, parts 420 and 430 form a tortuous path from inside to outside of the clam shell. Such paths are commonly used to provide environmental protection to maintain sterility of medical parts.

Further, proximally facing surfaces 434 and 436 of parts 430 and 420, respectively, are contoured to form a seal against distally facing edges 440 and 442 of hub 352 (see FIG. 23). In this manner, blade 90' is fully protected while disposed within a closed clamshell formed by parts 420 and 430. To further assure blade 90' sterility, joining sections of hub 352 and parts 420 and 430 may be coated and sealed with a fracturable material, such as a thin coating of acrylic.

For further assurance of maintaining blade 90' sterility, part 430 has a raised protuberance 444. Cooperatively, housing 300 has a distally disposed section 450 (see FIG. 17) having a pair of inwardly disposed walls 452 and 454 which compressively force parts 420 and 430 tightly together while parts 420 and 430 are disposed in respective contact with walls 454 and 452 (see FIG. 17). Also, each wall 452 and 454 comprises an indent 456 which conforms in size and position with protuberance 444 to provide a releasible detent which aid in maintaining parts 420 and 430 in closed relationship until removed by actuation of lancet 10'. Note that it is well known in the art to mold such detents into a part while using a straight pull orthogonal to the detent when injection molding using a pliable material such as polypropylene. Having a detent in each wall 452 and 454 permits assembly of parts of lancet 10' in either a 0° or 180° orientation of housing 300 relative to the other two assembled molded parts 310 and 320.

One of the salient features of lancet 10' is the process involved in its manufacture. All three parts of lancet 10' are produceable by single, straight pull injection molding. It is preferable that blade 90' be insert molded into actuator and blade assembly 320. Such insert molding is well known and commonly done in lancet blade part manufacture.

Figure 24:
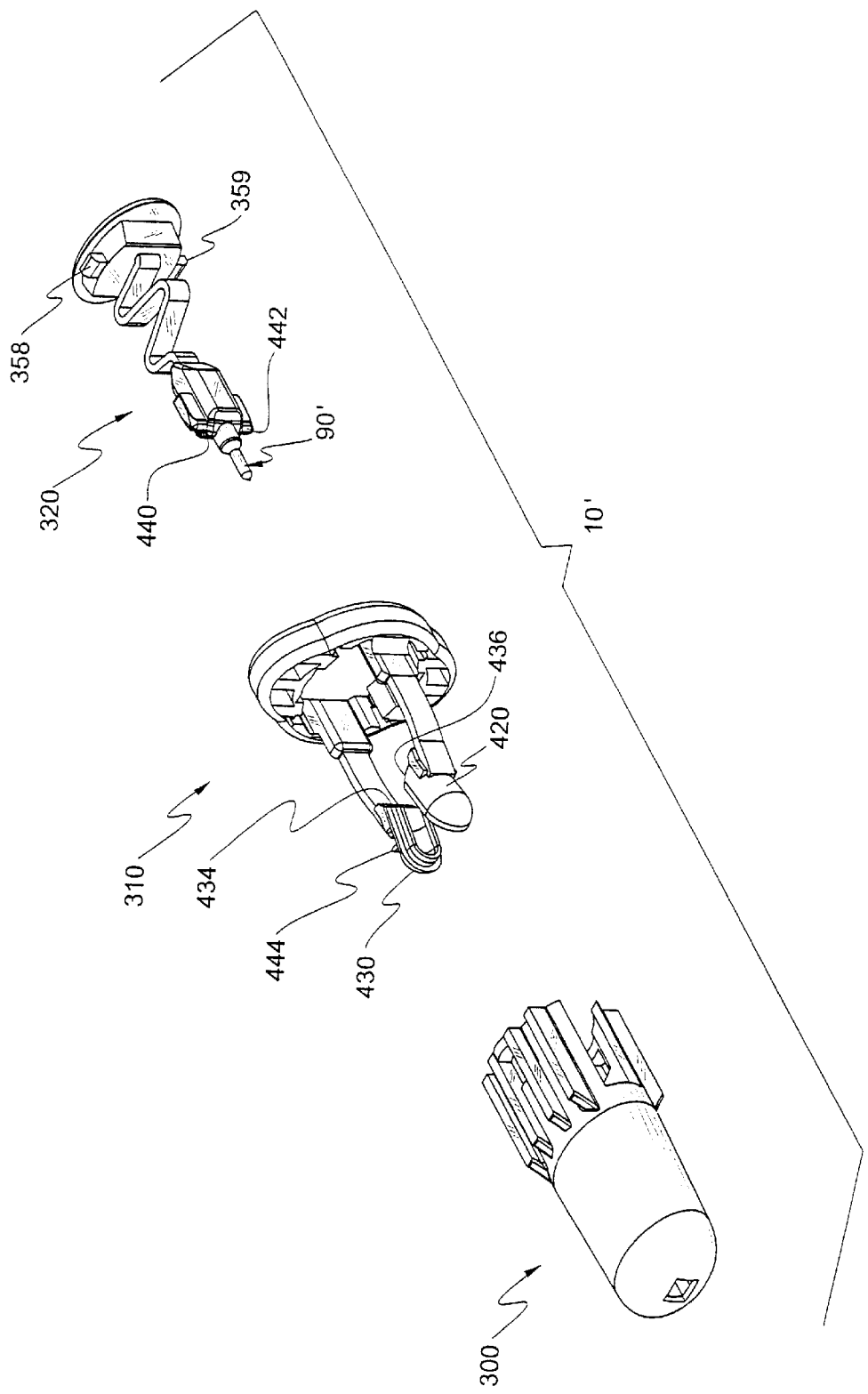
FIG. 24 is an exploded perspective of parts which make-up the second lancet embodiment.

Referring to FIG. 24, it may be noted that assembly of lancet 10' is also a linear process. Actuator and blade assembly 320 is simply inserted into ring/blade shield assembly 310 until blade 90' is disposed within the clamshell region provided by parts 420 and 430 and distally facing edges 440 and 442 are disposed in close relation with proximally facing surfaces 434 and 436 of parts 430 and 420, respectively. Facing surfaces 434 and 436 are best seen in FIG. 22.

Subsequently, so assembled actuator and blade assembly 320 and ring/blade shield assembly 310 are linearly inserted into housing 300 until protuberance 444 is engaged into an indent 456 (see FIG. 17). See FIG. 17. So assembled, lancet 10' is ready for sterilization, then shipment, storage and use without additional packaging.

Figure 17:
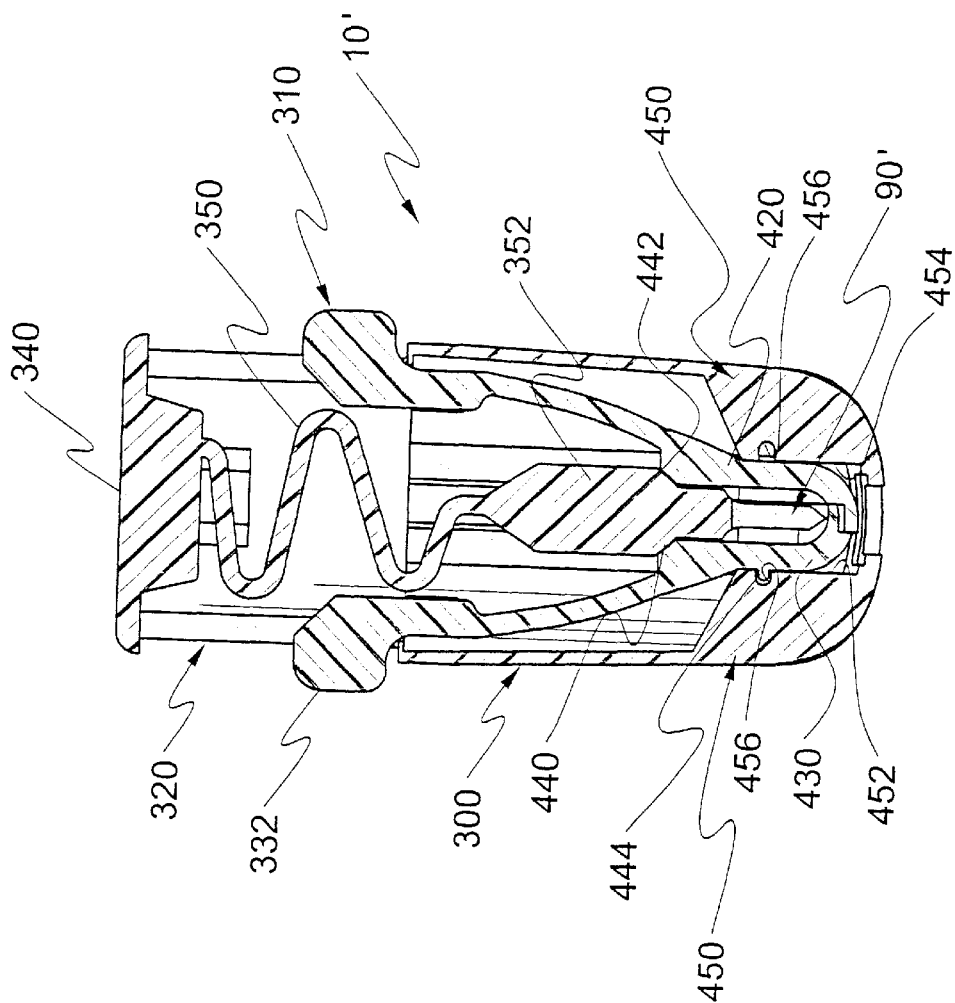
FIG. 17 is a cross section cut along lines 17—17 of FIG. 16.
Figure 18:
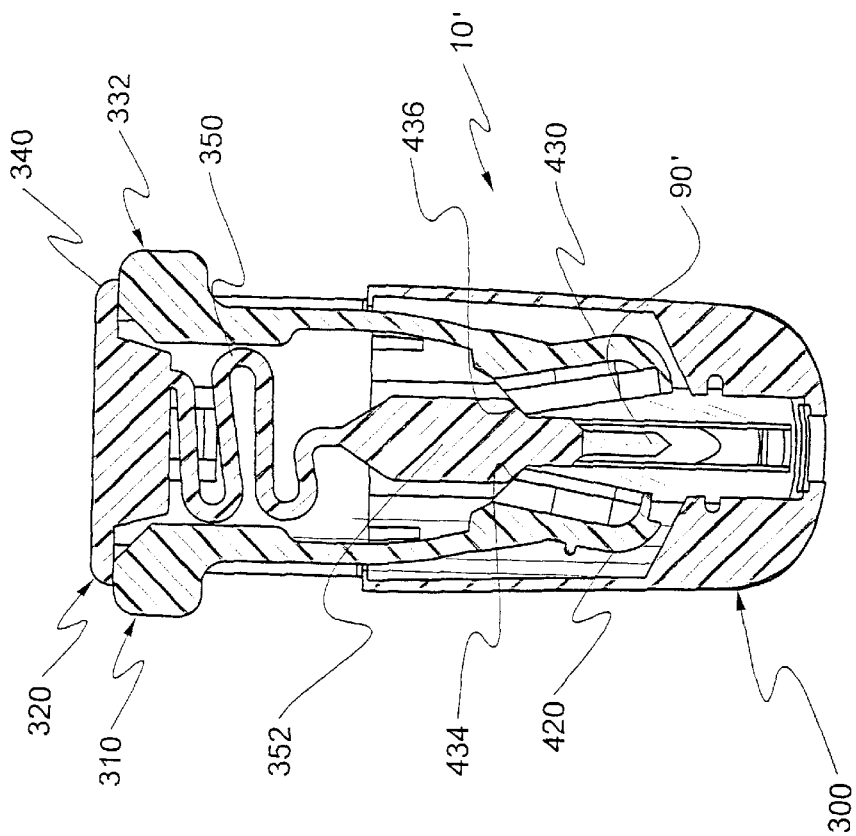
FIG. 18 is a cross section, similar to the cross section of FIG. 17 but with the actuator and blade assembly displaced relative to the housing and ring/blade shield assembly to compress and store energy in a spring associated with the actuator and blade assembly during a portion of a lancet firing cycle.
Figure 19:
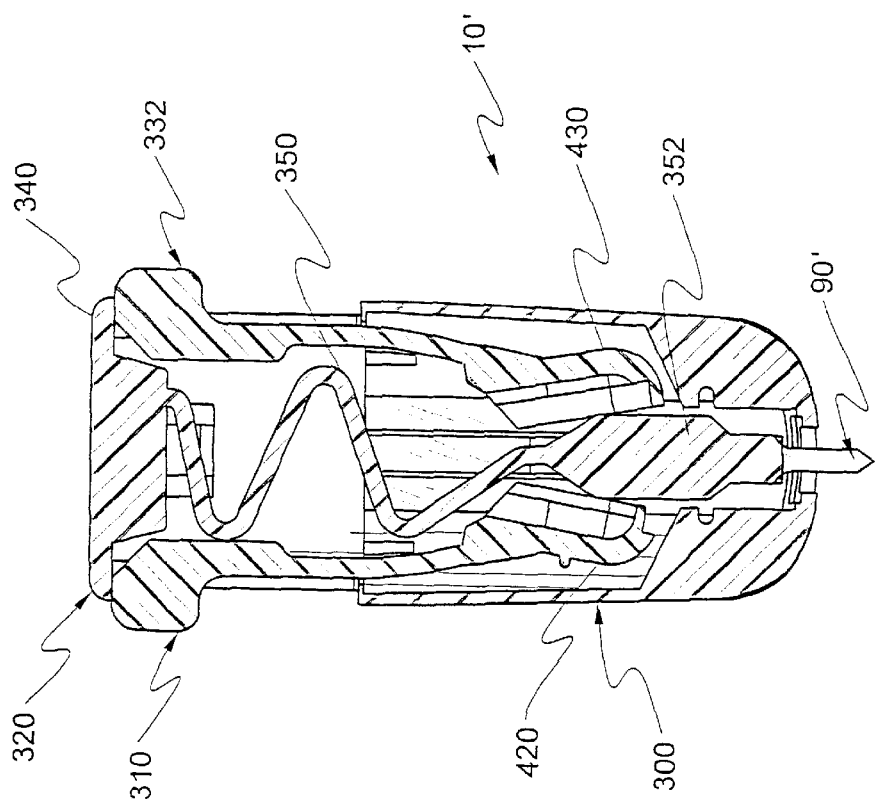
FIG. 19 is a cross section, similar to the cross section of FIG. 18, wherein release of energy stored within the spring results in spring over travel and consequential lancet blade travel outside the housing.
Figure 20:
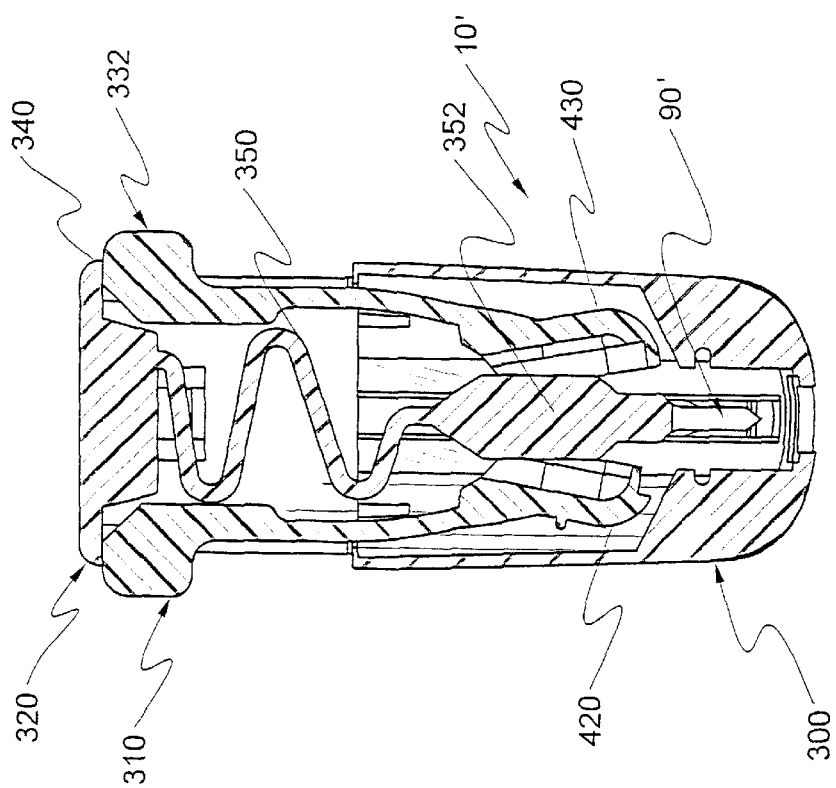
FIG. 20 is a cross section, similar to the cross section of FIG. 19, wherein contraction of the spring to a rest state retracts the lancet blade into safety of the housing.

Exemplary steps in a complete lancing cycle is provided in FIGS. 17–20. The preactuation state of lancet 10' is seen in FIG. 17 where lancet blade 90' is aseptically confined within displaceable shield 330. To actuate lancet 10', actuator ring 332 is displaced toward actuator button 340 compressing spring 350 to a point just prior to release of hub 352 to activate lancet 10', as seen in FIG. 18. Parts 420 and 430 are forced apart by action of hub 352 against facing surfaces 434 and 436. This continues until parts 420 and 430 are sufficiently far displaced to release hub 352.under force of spring 350. As seen in FIG. 19, over travel of spring 350 drives lancet blade 90! distally outward from housing 300 in a lancing action. At the end of the lancing cycle, spring 350 recoils to retract blade 90' into safety of housing 300 as seen in FIG. 20.

While lancet 10' models have been made and successfully tested, a potential element of unreliability is exacting control of release of hub 352 at the time spring 350 is properly compressed. For this purpose, a third embodiment of the present invention, lancet 10", is disclosed, as seen in cross section in FIGS. 25 and 26. In all ways, lancet 10" is substantially the same as lancet 10', except for a pair of beams 460 and 462 of an actuator and blade assembly 320' extending distally from actuator button 340, curvature of elongated legs, numbered 400' and 410', of a ring/blade shield assembly 310', angles of interaction between a hub 352' and facing surfaces 434' and 436' of actuator and blade assembly 320' and width of housing 300'.

Note that each elongated leg 400' and 410' comprises a linear section 470 and 472, respectively, and an inwardly curving section 474 and 476, respectively. Housing 300' is increased in width to accommodate additional space required by beams 460 and 462. As seen in FIG. 25, facing surfaces 434' and 436' and related parts of parts hub 352' are more nearly orthogonal to direction of displacement of blade 90' than similar parts of lancet 10'.

For this reason, displacement of hub 352' as spring 350 is compressed, does not by itself cause parts 420' and 430' to separate and ultimately release hub 352' to activate lancet 10". Instead, separating forces upon parts 420' and 430' are the result of beams 460 and 462 contacting inwardly curving sections 474 and 476, respectively. This contact causes parts 4201 and 430' to separate and release lancet blade 90' to permit decompression of spring 350, thereby initiating a lancing cycle.

Note, in FIG. 26, inwardly curving sectons 474 and 476 are displaced outwardly to separate parts 420' and 430' to until hub 352' is ultimately released to activate blade 90', initiating the lancing cycle. Completion of the lancing cycle of lancet 10" is substantially the same as the latter portions of the lancing cycle of lancet 10', as seen in FIGS. 19 and 20.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by letters patent is:

1. A self-contained lancet which requires but one operational step to perform a lancing procedure, said lancet comprising:
   a housing comprising an elongated contiguous side wall which surrounds and shelters lancet parts residing within said housing, said housing further comprising a substantially open first end wherethrough an actuator is unidirectionally displaced to energize and activate a lancing cycle and a slot on the other end through which a lancet blade is displaced;
   the lancet blade, disposed for transport before use and for disposal after use, within said housing;
   a covering, removed as a part of the single operational step, being protectively disposed to provide a sterile encasement about the lancet blade before use, said cover maintaining the lancet blade in an uncontaminated state until the lancet is uncovered during the single operational step;
   the actuator which is displaceable from a first state whereat digital access is provided toward and to a second state whereby the lancet is activated;
   an energy storing member which communicates with the actuator at a first site and is securely affixed to the lancet blade at a second site and which stores energy during a first portion of actuator displacement from the first state to the second state and released during a second portion of actuator displacement from the first state to the second state to discharge the lancet outward from the housing and then to return the lancet to protective safety of the housing; and
   a stripping apparatus which separates the lancet blade from the removable covering during the first portion of actuator displacement.

2. A self-contained lancet according to claim 1 further comprising apparatus for sweeping undesirable material within said housing from the region of said slot to clear an unobstructed pathway for said lancet blade.

3. A self-contained lancet according to claim 1 wherein said actuator and said energy storing member are formed as a single integrated part.

4. A self-contained lancet according to claim 1 wherein said removable covering and a portion of said stripping apparatus are formed as a single integrated part.

5. A method for using a self-contained lancet which requires but one operational step to perform a lancing procedure, comprising the steps of:
   providing a lancet comprising:
      a housing comprising an elongated contiguous side wall which surrounds and shelters lancet parts residing within said housing, said housing further comprising an open first end wherethrough an actuator is unidirectionally displaced to energize and activate a lancing cycle and a slot on the other end through which a lancet blade is displaced;
      the lancet blade, disposed for transport before use and for disposal after use, within said housing;
      a lancet blade covering, removable by action of the single operational step, being protectively disposed to provide a sterile encasement about the lancet blade before use, said cover maintaining the lancet blade in an uncontaminated state until the lancet is uncovered therefrom;
      the actuator which is displaceable from a first state whereat digital access is provided toward and to a second state whereby the lancet is activated;
      an energy storing member which communicates with the actuator at a first site and is securely affixed to the lancet blade at a second site and which stores energy during a first portion of actuator displacement from the first state to the second state and released during a second portion of actuator displacement from the first state to the second state to discharge the lancet outward from the housing and then to return the lancet to protective safety of the housing; and
      a stripping apparatus which separates the lancet blade from the removable covering during the first portion of displacement of the actuator;
   displacing the actuator unidirectionally from the first state to the second state thereby storing energy in the energy storing member and separating the lancet blade from the removable covering during the first portion of actuator displacement from the first state to the second state and then releasing the energy storing member during the second portion of actuator displacement from the first state to the second state to discharge the lancet from the housing and return the lancet into the housing.

6. A method for using a self-contained lancet according to claim 5 comprising the further steps of providing apparatus for sweeping undesirable material within said housing from the region of said slot to clear an unobstructed pathway for said lancet blade and sweeping unwanted material from the region of said slot during the first portion of displacement of the actuator from the first state to the second state.

* * * * *